(12) United States Patent
Cuevas

(10) Patent No.: US 9,204,961 B2
(45) Date of Patent: Dec. 8, 2015

(54) METHOD OF IMPLANTING AN INTRAOCULAR DEVICE TO INHIBIT CELL MIGRATION AND OPACIFICATION OF THE POSTERIOR CAPSULE OF THE EYE

(71) Applicant: InSight Innovations, LLC, Denver, CO (US)

(72) Inventor: Kevin H. Cuevas, Denver, CO (US)

(73) Assignee: Insight Innovations, LLC, Denver, CO (US)

( * ) Notice: Subject to any disclaimer, the term of this patent is extended or adjusted under 35 U.S.C. 154(b) by 22 days.

(21) Appl. No.: 13/944,817

(22) Filed: Jul. 17, 2013

(65) Prior Publication Data

US 2013/0304205 A1    Nov. 14, 2013

Related U.S. Application Data

(63) Continuation of application No. 13/479,178, filed on May 23, 2012, which is a continuation-in-part of application No. 13/136,515, filed on Aug. 2, 2011, now Pat. No. 8,551,167, which is a
(Continued)

(51) Int. Cl.
*A61F 2/16* (2006.01)
*A61L 27/38* (2006.01)
*A61L 27/58* (2006.01)
(Continued)

(52) U.S. Cl.
CPC ... *A61F 2/16* (2013.01); *A61F 2/14* (2013.01); *A61F 2/161* (2015.04); *A61F 2/1624* (2013.01); *A61L 27/3869* (2013.01); *A61L 27/58* (2013.01); *A61F 2002/009* (2013.01); *A61L 2430/16* (2013.01)

(58) Field of Classification Search
CPC ....... A61F 2/16; A61F 2/1613; A61F 2/1664; A61F 2/1648; A61F 2/1635; A61F 2/1662; A61F 2/14; A61F 2/1602; A61F 2002/161; A61F 2002/1697; A61F 2230/0065; A61F 2250/0053; A61F 2250/0058; A61F 2250/0067
USPC ........................ 623/6.14–6.17, 6.44, 6.4, 6.41
See application file for complete search history.

(56) References Cited

U.S. PATENT DOCUMENTS 3,794,414 A * 2/1974 Wesley .................... 351/159.41
3,960,150 A   6/1976 Hussain et al.
(Continued)

FOREIGN PATENT DOCUMENTS

EP   1402851   3/2004
EP   2305178   4/2011
(Continued)

OTHER PUBLICATIONS

European Patent Application No. 12820279.3; Office Action dated Jan. 27, 2015, 10 total pages.
(Continued)

*Primary Examiner* — Paul Prebilic
(74) *Attorney, Agent, or Firm* — Craig R. Miles; CR Miles P.C.

(57) ABSTRACT

Generally, an intraocular implant and methods for treating an ocular condition. In particular, an intraocular implant which implanted between an intraocular lens and the surface of the posterior capsule of the eye inhibits migration of residual lens epithelial cells after cataract surgery by providing structural barriers to reduce posterior capsule opacification of the eye.

22 Claims, 14 Drawing Sheets

Related U.S. Application Data continuation-in-part of application No. 12/998,652, filed as application No. PCT/US2009/006195 on Nov. 19, 2009.

(60) Provisional application No. 61/270,567, filed on Jul. 10, 2009, provisional application No. 61/199,674, filed on Nov. 20, 2008.

(51) Int. Cl.
*A61F 2/14* (2006.01)
*A61F 2/00* (2006.01)

(56) References Cited

U.S. PATENT DOCUMENTS

| | | | |
|---|---|---|---|
| 4,014,335 A | 3/1977 | Arnold | |
| 4,179,497 A | 12/1979 | Cohen et al. | |
| 4,441,217 A | 4/1984 | Cozean, Jr. | |
| 4,624,669 A | 11/1986 | Grendahl | |
| 4,808,181 A | 2/1989 | Kelman | |
| 4,865,601 A | 9/1989 | Caldwell et al. | |
| 5,098,443 A | 3/1992 | Parel et al. | |
| 5,275,624 A * | 1/1994 | Hara et al. | 623/6.41 |
| 5,354,331 A * | 10/1994 | Schachar | 623/4.1 |
| 5,405,285 A | 4/1995 | Hirano et al. | |
| 5,405,385 A | 4/1995 | Heimke et al. | |
| 5,443,505 A | 8/1995 | Wong et al. | |
| 5,501,856 A | 3/1996 | Ohroti et al. | |
| 5,549,670 A | 8/1996 | Young et al. | |
| 5,618,553 A | 4/1997 | Kelleher | |
| 5,628,795 A | 5/1997 | Langerman | |
| 5,800,533 A * | 9/1998 | Eggleston et al. | 623/6.39 |
| 6,063,116 A | 5/2000 | Kelleher | |
| 6,063,396 A | 5/2000 | Kelleher | |
| 6,551,354 B1 * | 4/2003 | Ghazizadeh et al. | 623/6.43 |
| 6,554,424 B1 | 4/2003 | Miller et al. | |
| 6,616,691 B1 | 9/2003 | Tran | |
| 6,713,081 B2 | 3/2004 | Robinson et al. | |
| 6,797,004 B1 * | 9/2004 | Brady et al. | 623/6.4 |
| 6,932,839 B1 | 8/2005 | Kamerling et al. | |
| 6,972,033 B2 * | 12/2005 | McNicholas | 623/6.37 |
| 7,025,783 B2 | 4/2006 | Brady et al. | |
| 7,037,337 B2 | 5/2006 | Carriazo | |
| 7,117,807 B2 | 10/2006 | Bohn, Jr. et al. | |
| 7,143,709 B2 | 12/2006 | Brennan et al. | |
| 7,435,258 B2 | 10/2008 | Blake | |
| 7,491,350 B2 | 2/2009 | Silvestrini | |
| 7,650,848 B2 | 1/2010 | Brennan et al. | |
| 8,287,592 B2 | 10/2012 | Silvestrini | |
| 8,303,655 B2 | 11/2012 | Basoglu et al. | |
| 8,308,800 B2 | 11/2012 | Chu | |
| 2001/0034552 A1 | 10/2001 | Young et al. | |
| 2002/0010510 A1 | 1/2002 | Silvestrini | |
| 2003/0144733 A1 | 7/2003 | Brady et al. | |
| 2003/0149479 A1 | 8/2003 | Snyder et al. | |
| 2004/0042073 A1 | 3/2004 | Pynson | |
| 2004/0236423 A1 | 11/2004 | Zhang et al. | |
| 2004/0243231 A1 | 12/2004 | Koziol | |
| 2005/0033420 A1 | 2/2005 | Christie et al. | |
| 2006/0064161 A1 | 3/2006 | Blake | |
| 2006/0118263 A1 * | 6/2006 | Silvestrini | 164/46 |
| 2006/0235514 A1 | 10/2006 | Silvestrini | |
| 2006/0235515 A1 | 10/2006 | Chassain | |
| 2007/0083260 A1 | 4/2007 | Colvard | |
| 2007/0106381 A1 | 5/2007 | Blake | |
| 2008/0077238 A1 | 3/2008 | Deacon et al. | |
| 2008/0077239 A1 | 3/2008 | Zickler et al. | |
| 2008/0241223 A1 | 10/2008 | Nivaggioli et al. | |
| 2009/0234448 A1 | 9/2009 | Weeber et al. | |
| 2010/0126404 A1 | 5/2010 | Brennan et al. | |
| 2010/0226943 A1 | 9/2010 | Brennan et al. | |
| 2011/0040376 A1 * | 2/2011 | Christie et al. | 623/6.17 |
| 2011/0098808 A1 | 4/2011 | Kobayashi et al. | |
| 2011/0230963 A1 | 9/2011 | Cuevas | |
| 2011/0295367 A1 | 12/2011 | Cuevas | |
| 2012/0058302 A1 | 3/2012 | Eggenspieler et al. | |
| 2012/0232649 A1 | 9/2012 | Cuevas | |
| 2013/0053953 A1 | 2/2013 | Silvestrini | |
| 2013/0053954 A1 * | 2/2013 | Rao et al. | 623/6.13 |
| 2013/0153612 A1 | 6/2013 | O'Brien et al. | |

FOREIGN PATENT DOCUMENTS

| | | |
|---|---|---|
| FR | 2 832 920 A1 | 6/2003 |
| WO | 93/09732 | 5/1993 |
| WO | 2008/108523 | 9/2008 |
| WO | WO 2010/059214 | 5/2010 |
| WO | WO 2013/019871 | 2/2013 |

OTHER PUBLICATIONS

Leishman et al. Prevention of capsular bag opacification with a modified hydrophilic acrylic disk-shaped intraocular lens. J Cataract Refract Surg, Sep. 2012, 38, pp. 1664-1670.

Werner et al. Experimental evaluation of ophthalmic devices and solutions using rabbit models. Veterinary Ophthalmology, Sep. 2006, 9, 5, pp. 281-291.

Bluestein, et al. Dimensions of the Pediatric Crystalline Lens: Implications for Intraocular Lenses in Children. J Pediatr Ophthalmol Strabismus, Jan.-Feb. 1996, vol. 33, No. 1, pp. 18-20.

Menlyweb. Andre "the Giant" Roussimoff. Website, http://www.manlyweb.com, Dec. 2007, 3 total pages.

Noardi. Eye Size Chart. Website, http://www.noardi.net, Aug. 2013, 4 total pages.

Roarty, et al. Normal pupil size and anisocoria in newborn infants. Arch Ophthalmol, Jan. 1990, 108(1):94-95.

Melki et al. An implantable intraocular pressure transducer: Initial safety outcomes. JAMA Ophthalmology, Oct. 2014, vol. 132, No. 10, pp. 1221-1225.

Corresponding Mexican Patent Application No. MX/a/2011/005272; OA dated Mar. 27, 2014, 4 total pages.

Corresponding EP Patent Application No. 09827868.2; Response to OA filed Feb. 24, 2014, 17 total pages.

U.S. Appl. No. 61/199,674, filed Nov. 20, 2008.

U.S. Appl. No. 61/270,567, filed Jul. 10, 2009.

International Patent Cooperation Treaty Patent Application No. PCT/US2009/006195, filed Nov. 19, 2009.

International Patent Cooperation Treaty Patent Application No. PCT/US12/49176, filed Aug. 1, 2012.

International Patent Cooperation Treaty Patent Application No. PCT/US2013/041574, filed May 17, 2013.

Cleary et al. Effect of Square-edged Intraocular Lenses on Neodymium:YAG Laser Capsulotomy Rates in the United States. J. Cataract&Refractive Surgery, vol. 13, Nov. 2007, p. 1899-906.

Cortina et al. Diclofenac Sodium and Cyclosporine A Inhibit Human Lens Epithelial Cell Proliferation in Culture. Graefes Arch Clin Exp Ophthalmol, vol. 235, Mar. 1997, pp. 180-185.

Emery. Capsular Opacification After Cataract Surgery. Curr Opin in Ophthalmol, vol. 10, 1999, pp. 73-80.

Hara et al. Long-Term Study of Posterior Capsular Opacification Prevention With Endocapsular Equator Rings in Humans. Arch Ophthalmol, Jul. 2011, vol. 129(7), pp. 855-863.

Hartmann et al. Prevention of Secondary Cataract by Intracapsular Administration of the Antibiotic Daunomycin. Ophthalmol, vol. 4, Jan. 1990, pp. 102-106.

Inan et al. Effect of Diclofenac on Prevention of Posterior Capsule Opacification in Human Eyes. Can J Ophthalmol, vol. 41, Oct. 2006, pp. 624-629.

Inan et al. Prevention of Posterior Capsule Opacification by Retinoic Acid and Mitomycin. Graefes Arch Clin Exp Ophthalmol, vol. 239, Aug. 2001, pp. 693-697.

Inan et al. Prevention of Posterior Capsule Opacification by Intraoperative Single-dose Pharmacologic Agents. J Cataract Refract Surg, Jul. 2001, vol. 27, pp. 1079-1087.

Ismail et al. Prevention of Secondary Cataract by Antimitotic Drugs: Experimental Study. Ophthalmic Res, 1996, vol. 28(1), pp. 64-69.

(56) References Cited

OTHER PUBLICATIONS

Kavoussi, et al. Prevention of Capsular Bag Opacification with a New Hydrophilic Acrylic Disk-Shaped Intraocular Lens.J Cataract Refract Surg, Dec. 2011, 37, pp. 2194-2200.

Maloof et al. Selective and Specific Targeting of Lens Epithelial Cells During Cataract Surgery Using Sealed-Capsule Irrigation J. Cataract Refract Surg, Aug. 2003, vol. 29, pp. 1566-1568.

J Cataract Refract Surg, Aug. 2003, vol. 29, pp. 1566-1568.

Oberleithner et al. Fusion of renal epithelial cells: A model of studying cellular mechanisms of ion transport. Proc. Natl. Acad. Sci. USA, May 1986, vol. 83, pp. 3547-3551.

Osnsupersite. New Accommodating IOL Offers High Rate of Spectacle Independence; Website, http://www.osnsupersite.com, originally downloaded Apr. 4, 2012, 3 total pages.

Sharklet Technologies, Inc. Website, http://www.sharklet.com, originally downloaded Aug. 2, 2011, 11 total pages.

Tekia. Website, http://tekia.com, originally downloaded Apr. 4, 2012, 1 page.

U.S. Appl. No. 12/998,652, filed May 13, 2011; OA mailed Aug. 7, 2012.

U.S. Appl. No. 12/998,652, filed May 13, 2011; OA mailed Aug. 27, 2012.

U.S. Appl. No. 12/998,652, filed May 13, 2011; OA mailed Mar. 18, 2013.

U.S. Appl. No. 13/136,515, filed Aug. 2, 2011; OA mailed Dec. 17, 2012.

U.S. Appl. No. 13/136,515, filed Aug. 2, 2011; OA mailed Feb. 13, 2013.

Corresponding EP patent application No. 09827868.2; OA mailed Mar. 6, 2013, 7 total pages.

* cited by examiner

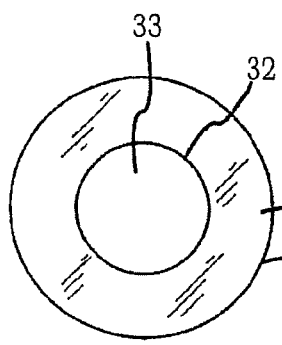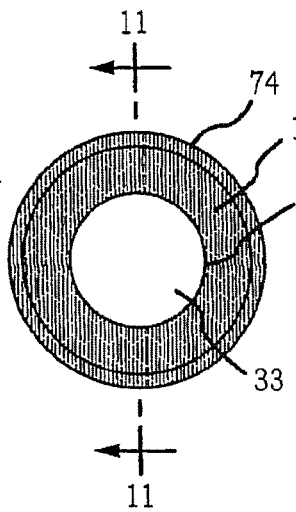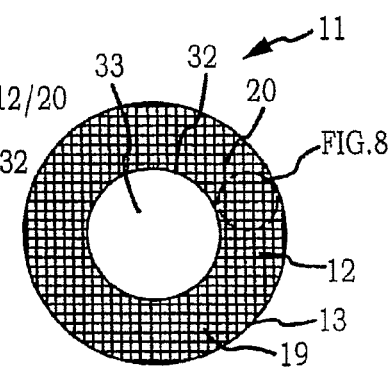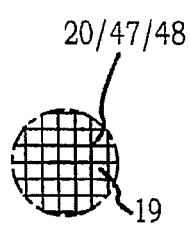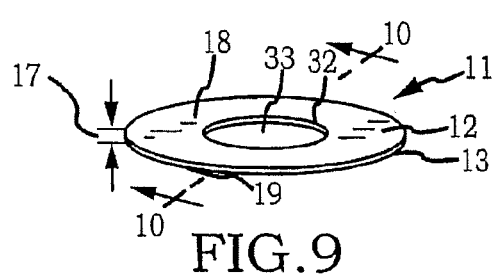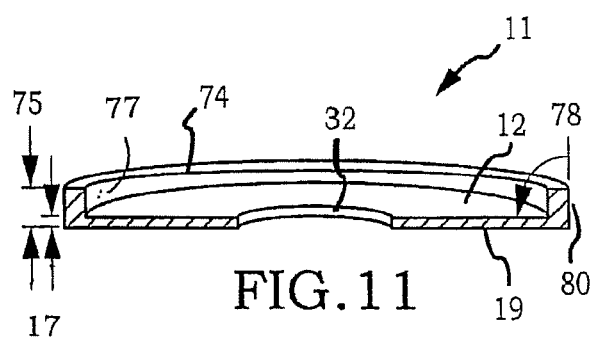

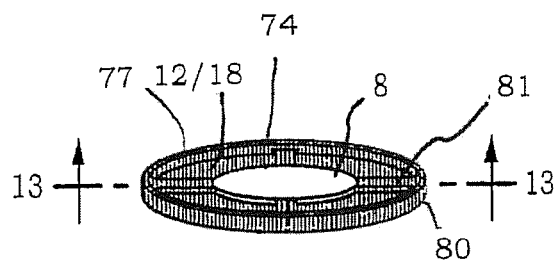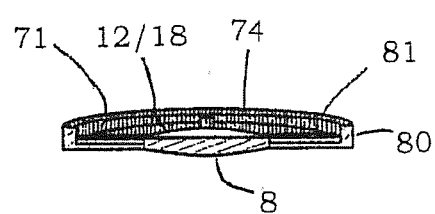
FIG.12  FIG.13
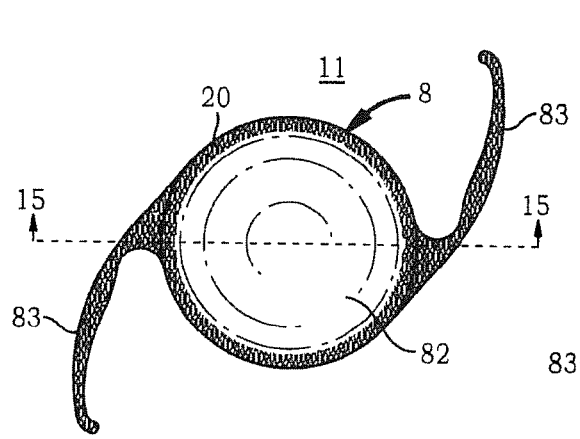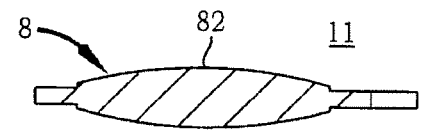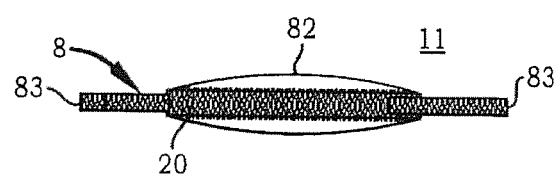
FIG. 14  FIG. 15
FIG. 16

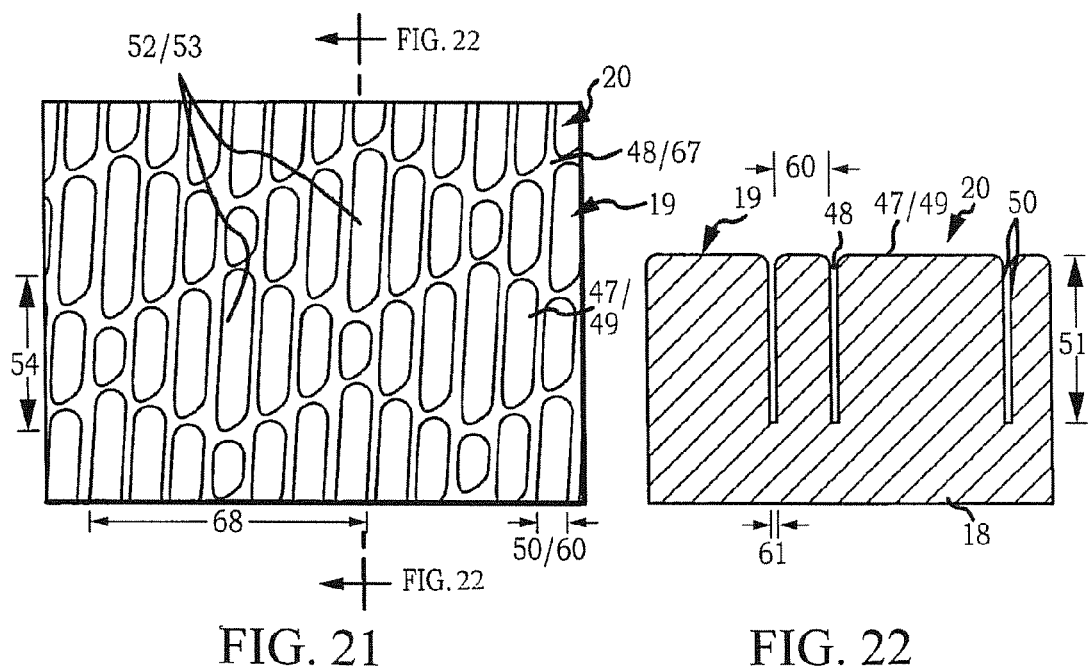
FIG. 21
FIG. 22
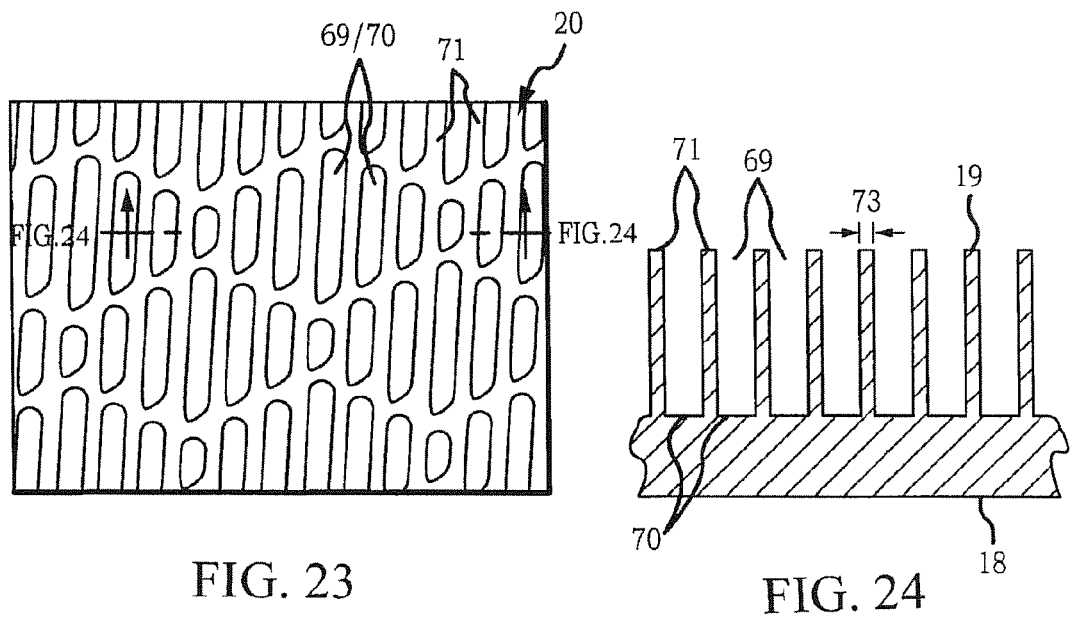
FIG. 23
FIG. 24

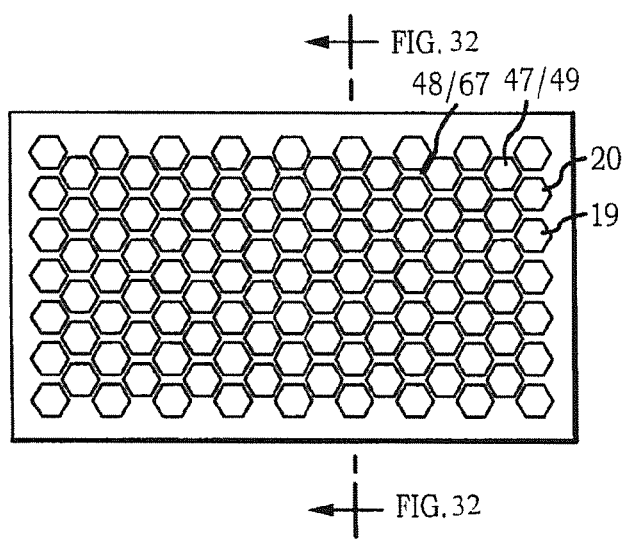
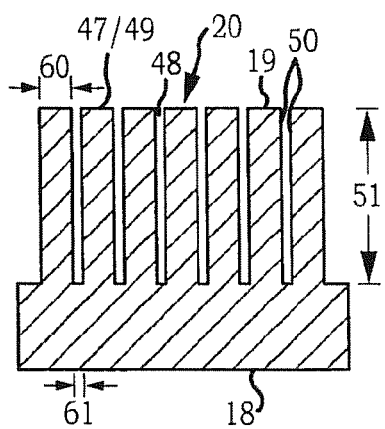
FIG. 31  FIG. 32
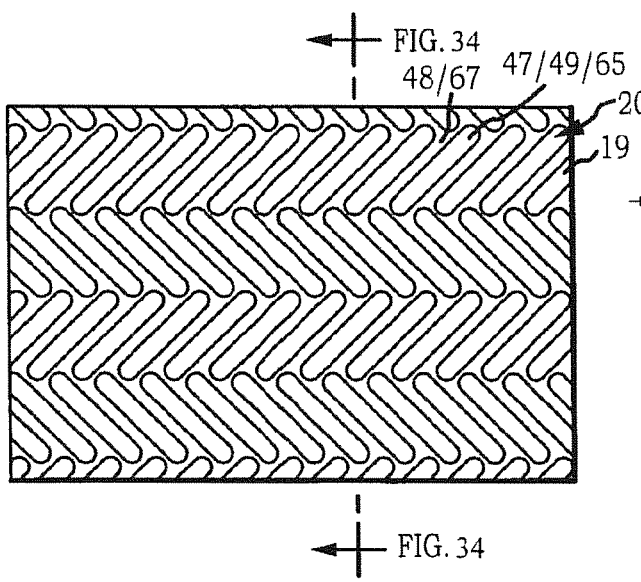
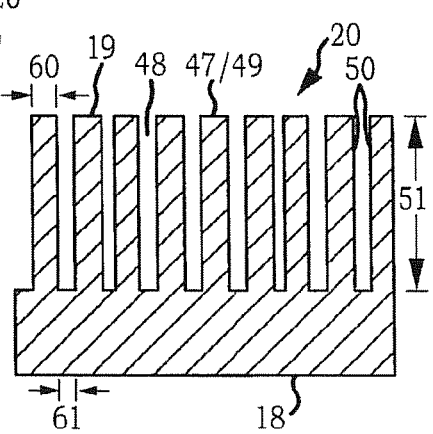
FIG. 33  FIG. 34

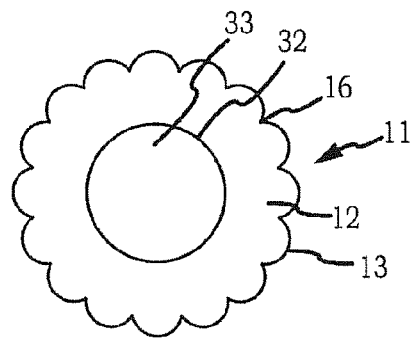
FIG. 35
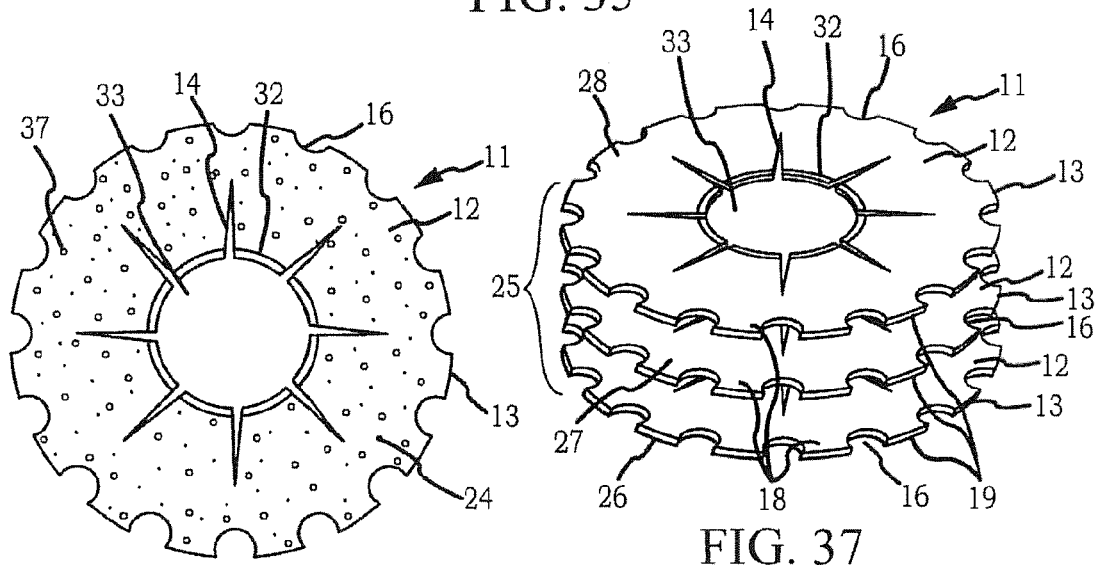
FIG. 36
FIG. 37
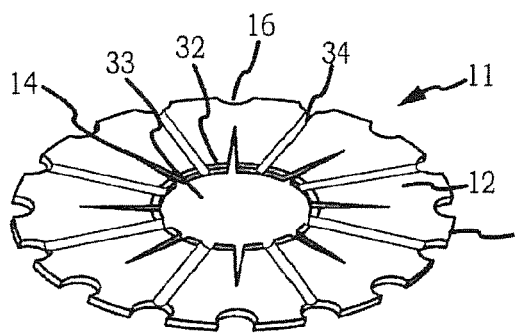
FIG. 38
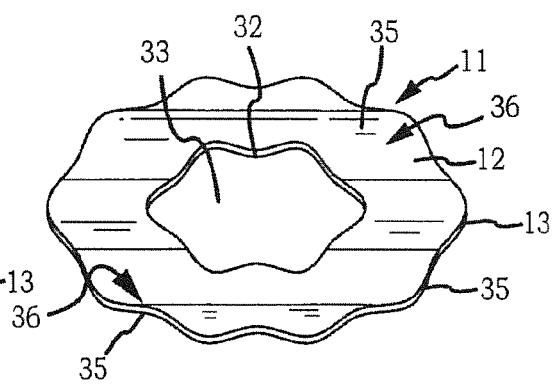
FIG. 39

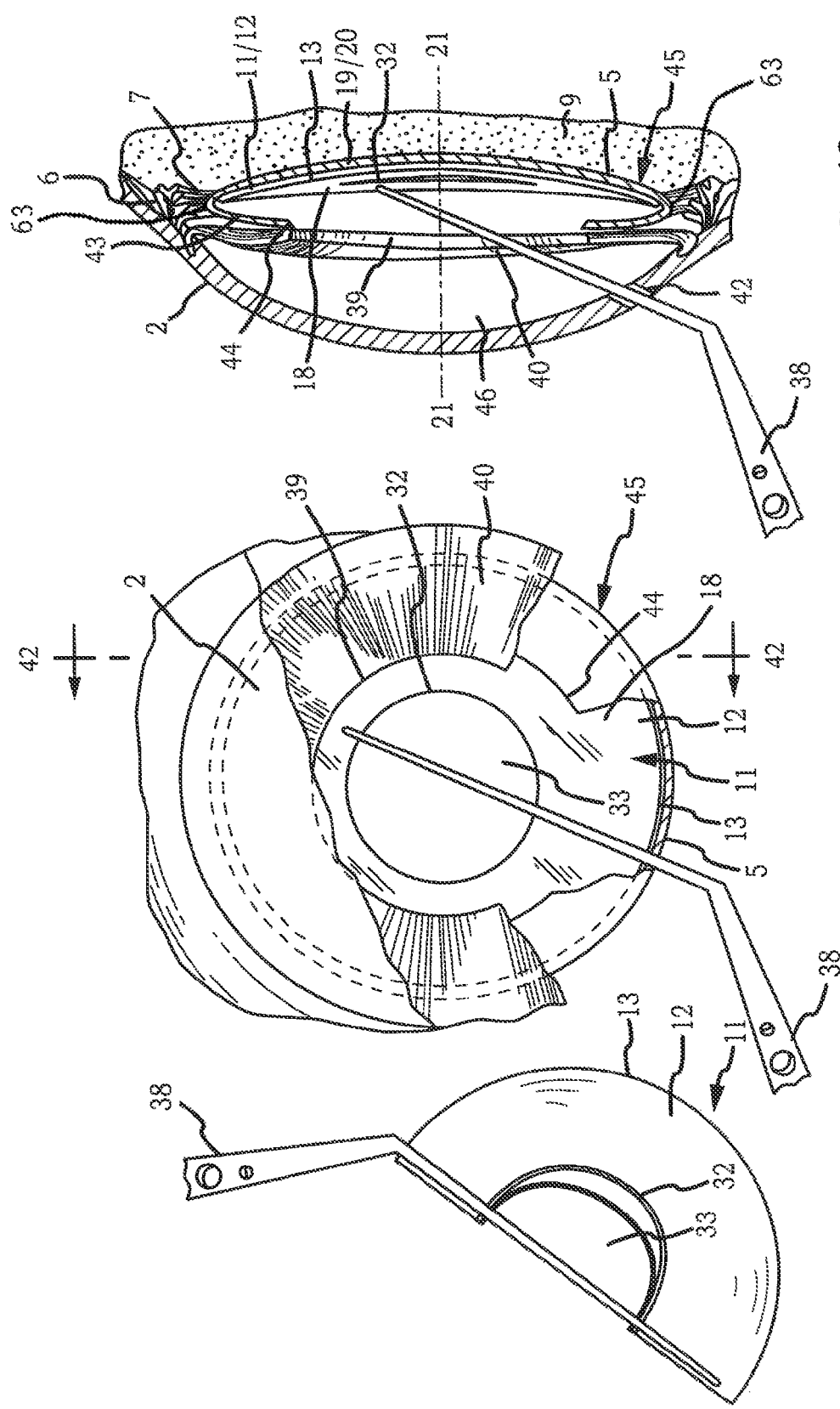

METHOD OF IMPLANTING AN INTRAOCULAR DEVICE TO INHIBIT CELL MIGRATION AND OPACIFICATION OF THE POSTERIOR CAPSULE OF THE EYE

This United States patent application is a continuation of U.S. patent application Ser. No. 13/479,178, filed May 23, 2012, now abandoned, which is a continuation-in-part of U.S. patent application Ser. No. 13/136,515, filed Aug. 2, 2011, now U.S. Pat. No. 8,551,167, which is a continuation-in-part of U.S. patent application Ser. No. 12/998,652, filed May 13, 2011, which is a United States National Stage of International Patent Cooperation Treaty Patent Application No. PCT/US2009/006195, filed Nov. 19, 2009, which claims the benefit of U.S. Provisional Patent Application 61/270,567, filed Jul. 10, 2009 and U.S. Provisional Patent Application No. 61/199,674, filed Nov. 20, 2008, each hereby incorporated by reference herein.

I. TECHNICAL FIELD

Generally, an intraocular implant and methods for treating an ocular condition. In particular, an intraocular implant which implanted between an intraocular lens and the surface of the posterior capsule of the eye inhibits migration of residual lens epithelial cells after cataract surgery by providing structural barriers to reduce posterior capsule opacification of the eye.

II. BACKGROUND

Visually impairing cataract is the leading cause of preventable blindness in the world. Presently, the only known treatment for cataract is the surgical removal of the opacified lens of the affected eye and replacement with an artificial intraocular lens, typically including an intraocular lens optic and haptics ("IOL"). Technological advances in cataract surgery with IOL implantation have made cataract surgery among the most effective surgical procedures.

Now referring primarily to FIGS. 1 and 2, which show a top view and a cross section view of a phakic eye (1). The most common technique of cataract surgery may be extracapsular cataract extraction ("ECCE") which involves the creation of an incision (42) near the outer edge of the cornea (2) and a circular opening (44)(shown in FIGS. 3 and 4) in the anterior lens capsule (43)(also herein referred to as the "anterior capsule") through which the opacified lens (3) can be removed from the lens capsule (45)(also referred to as the "capsular bag"). Now referring primarily to FIGS. 3 and 4 which show a top view and a cross section view of a pseudophakic eye (4), the lens capsule (45) anchored to the ciliary body (6) through the zonular fibers (7) can be left substantially intact. The IOL (8) can then be placed within the lens capsule (45) through the circular opening (44) in the anterior capsule (43). The IOL (8) can be acted on by zonular forces exerted on the outer circumference (63) of the lens capsule (45) which establishes the location of the IOL (8) within the lens capsule (45). The intact posterior capsule (5) acts as a barrier to the vitreous humor (9) within the posterior segment of the eye.

The most frequent complication to ECCE and other methods of cataract surgery can be opacification of the posterior capsule (5). Posterior capsule opacification ("PCO") results from the migration of residual lens epithelial cells ("LEC") between the IOL (8) and the surface of the posterior capsule (5) subsequent to cataract surgery. The residual LECs once located between the IOL (8) and the surface of the posterior capsule (5) can proliferate leading to clouding of the normally clear posterior capsule (5). Clouding of the posterior capsule (5) can decrease visual acuity if the opacification occurs within the visual axis (21).

Visually significant PCO requires an additional surgery to clear the visual axis of the eye. Presently, the most widely utilized procedure to clear the visual axis of PCO may be Neodymium: Yttrium-Aluminum-Garnet ("Nd:YAG") laser capsulotomy. However, there may be substantial problems with this procedure such as IOL damage, postoperative intraocular pressure spikes, vitreous floaters, cystoid macular edema, retinal detachment, and IOL subluxation, or the like. Additionally, pediatric patients can be difficult to treat and a delay in treatment can lead to irreversible amblyopia. Many underdeveloped countries do not have access to a Nd:YAG laser and the cost can be prohibitive.

Prevention or inhibition of PCO fall into two broad categories: mechanical and pharmacological. Mechanical mechanisms to inhibit PCO have primarily focused on configuration of the IOL (8). Configuring the IOL to include a sharp posterior edge may provide a structural barrier to the migration of residual LECs between the IOL and the surface of the posterior capsule (5). Cleary et al., *Effect of Square-edged Intraocular Lenses on Neodymium: YAG Laser Capsulotomy Rates in the United States, J. Cataract & Refractive Surgery*, Vol. 33, p. 1899-1906 (November 2007). However, while introduction of square edged IOLs appears to have reduced incidence of PCO, a review of Medicare claims data from 1993 to 2003 evidences that the number of laser capsulotomies performed in the United States to treat PCO in recipients of square edged IOL remains substantial.

Pharmacological mechanisms have been proposed as a way to inhibit or prevent PCO. The effect of topical treatment with nonsteroidal anti-inflammatory drugs ("NSAIDs") such as diclofenac and indomethacin after phacoemulsification do not appear to inhibit PCO. Inan Man et al., *Effect of Diclofenac on Prevention of Posterior Capsule Opacification in Human Eyes, Can J Ophthalmol*, 41; 624-629 (2006). Additionally, the majority of pharmacological agents tested in-vitro for inhibition of migration and proliferation of LECs are antimetabolites and antimitotics which have not been used clinically because of their toxic side effects. Inan U U, Ozturk F, Kaynak S, et al. *Prevention of Posterior Capsule Opacification by Intraoperative Single-dose Pharmacologic Agents, J Cataract Refract Surg,* 27:1079-87(2001); Inan U U, Ozturk F, Kaynak S. Ilker S S, Ozer E, Güler, *Prevention of Posterior Capsule Opacification by Retinoic Acid and Mitomycin, Graefes Arch Clin Exp Ophthalmol* 239: 693-7(2001); Cortina P, Gomez-Lechon M J, Navea A, Menezo J L, Terencio M C, Diaz-Llopis, M, *Diclofenac Sodium and Cyclosporine A Inhibit Human Lens Epithelial Cell Proliferation in Culture, Graefes Arch Clin Exp Ophthalmol* 235: 180-5 (1997); Ismail M M, Alio J L, Ruiz Moreno J M, *Prevention of Secondary Cataract by Antimitotic Drugs: Experimental Study, Ophthalmic Res,* 28:64-9 (1996); Emery J., *Capsular Opacification After Cataract Surgery, Curr Opin Ophthalmol,* 10:73-80 (1999); Hartmann C, Wiedemann P, Gothe K, Weller M, Heimann K, *Prevention of Secondary Cataract by Intracapsular Administration of the Antibiotic Daunomycin, Ophthahnologie,* 4:102-6 (1990).

Also, available is a sealed capsule irrigation device which functions to allow selective irrigation of the lens capsule with LEC inhibiting pharmacologic agents. Maloof A J, Neilson G, Milverton E J, Pandy S K, *Selective and specific targeting of lens epithelial cells during cataract surgery using sealed-capsule irrigation, J Cataract Refract Surg,* 29:1566-68 (2003). It is not clear, however, that use of the device can be reduced to routine practice. Problems relating to incomplete seal of the lens capsule (45) resulting in leakage of potentially toxic chemicals into the anterior chamber (46) of the eye, rupture of the lens capsule (45) during manipulation of the irrigation device, difficulty in assessing kill of LECs within the lens capsule (45) and an increase in the duration of routine cataract surgery limit the usefulness of the irrigation device.

Another prominent problem with routine cataract surgery and other surgical procedures such as retinal surgery, cornea transplant surgery, glaucoma surgery, or the like, can be post-operative administration of antibiotics to prevent endophthalmitis. Topical antibiotic and anti-inflammatory eye drops represent the mainstay of drug delivery for intraocular surgery. However, there has yet to be a prospective randomized study showing that topical antibiotics prevent endophthalmitis. Also, because the human cornea acts as a natural barrier to biologic and chemical insults, intraocular bioavailability usually requires frequent dosing regimens for each medication. Topical drops can be difficult for young and elderly patients and the drop schedule can be cumbersome and confusing particularly when following surgery each eye is on a different drop schedule. These difficulties can result in non-compliance with serious consequences such as endophthalmitis, glaucoma, and cystoid macular edema. Recent prospective studies supporting the use of intracameral antibiotic injections for prophylaxis of endophthalmitis have stirred debate regarding the risks associated with this method of antibiotic prophylaxis including the short duration of protective effect (possibly less than 24 hours), the introduction of potentially contaminated substances in the anterior chamber, endothelial cell toxicity, toxic anterior segment syndrome, dilutional and osmolarity errors during mixing, and the like. Also, the systemic administration of drugs for treatment of localized ocular conditions may not be preferred because of the inefficiency associated with indirect delivery of the drugs to a target organ.

Recognizing these disadvantages of conventional delivery of antibiotics and other drugs to the eye, external ocular inserts were developed utilizing biologically inert materials to act as a reservoir for slow release of the drug. These external ocular inserts may be placed within the upper and lower conjunctival fornix of the eye to achieve a uniform sustained rate of release of drug in therapeutically effective amounts. However, patients can be intolerant of these devices due to difficulty in insertion and removal and mild to moderate conjunctival irritation during use which may explain why external ocular inserts have not been widely accepted in clinical practice.

III. DISCLOSURE OF INVENTION

Accordingly, a broad object of the invention can be to provide an intraocular implant having patterned surface elements which implanted between an intraocular lens and the surface of the posterior capsule of the eye provides a mechanical barrier which inhibits migration of residual lens epithelial cells after cataract surgery for treatment of an ocular condition.

Another broad object of the invention can be to provide a biocompatible intraocular implant and methods of treatment of an ocular condition by implantation of the biocompatible intraocular implant inside the eye with embodiments which can be intraocularly implanted in the posterior capsule of the eye to provide pharmaceutical barriers to interrupt progression of the ocular condition, the ciliary sulcus between the iris and the lens, or in the anterior chamber overlaying the iris.

Another broad object of the invention can be to provide a biocompatible intraocular implant locatable between the surface of the posterior capsule of the eye and an implanted IOL to provide a mechanical barrier which inhibits migration of residual lens epithelial cells after cataract surgery by providing structural barriers to reduce posterior capsule opacification of the eye.

Another broad object of the invention can be to provide a biocompatible biodegradable intraocular implant locatable between the surface of the posterior capsule of the eye and an implanted IOL to provide a biodegradable mechanical barrier for treatment of an ocular condition.

Another broad object of the invention can be to provide a biocompatible biodegradable intraocular implant locatable between the surface of the posterior capsule of the eye and an implanted IOL which combines a biocompatible biodegradable material which continually, or substantially continually, releases a therapeutically effective amount of an active agent to treat an ocular condition.

Another broad object of the invention can be to provide a biocompatible biodegradable intraocular implant locatable between the surface of the posterior capsule of the eye and an implanted IOL during cataract surgery which by structural or pharmaceutical barriers inhibits migration of residual lens epithelial cells to the surface of the posterior capsule.

Another broad object of the invention can be to provide a biocompatible biodegradable intraocular implant locatable between the surface of the posterior capsule of the eye and an implanted IOL during cataract surgery which by structural or pharmaceutical barriers inhibits proliferation of residual lens epithelial cells to the surface of the posterior capsule as a prophylaxis of PCO.

Another broad object of the invention can be to provide a biocompatible or biocompatible biodegradable intraocular implant locatable anterior to the natural crystalline lens or an implanted IOL within the ciliary sulcus for administration of one or more active agents.

Another broad object of the invention can be to provide a biocompatible or biocompatible biodegradable intraocular implant locatable in the anterior chamber overlaying the iris.

Naturally, further objects of the invention are disclosed throughout other areas of the specification, drawings, photographs, and claims.

IV. BRIEF DESCRIPTION OF THE DRAWINGS

FIG. 5 is a front view of a particular embodiment of the inventive intraocular implant of generally circular configuration.

FIG. 6 is a front view of a particular embodiment of the inventive intraocular implant of generally circular configuration which terminates radially in an annular member.

FIG. 7 is a back view of a particular embodiment of the inventive intraocular implant further providing patterned surface elements.

FIG. 8 is enlarged partial back view of the particular embodiment of the inventive intraocular implant shown in FIG. 6 providing patterned surface elements.

FIG. 9 is a perspective view of the particular embodiment of the inventive intraocular implant shown in FIG. 5.

FIG. 10 is a cross section view 10-10 of the particular embodiment of the inventive implant shown in FIG. 9.

FIG. 11 is a cross section view 11-11 of the particular embodiment of the inventive implant shown in FIG. 6.

FIG. 12 is a perspective view of a particular embodiment of the inventive intraocular implant.

FIG. 13 is a cross section view 13-13 of the particular embodiment of the inventive implant shown in FIG. 12.

FIG. 14 is plan view of a particular embodiment of the inventive intraocular implant.

FIG. 15 is a cross section view 15-15 of the particular embodiment of the inventive implant shown in FIG. 14.

FIG. 16 is a side view of the particular embodiment of the inventive implant shown in FIG. 14.

FIG. 21 is an enlarged partial back view of the particular embodiment of the inventive intraocular implant shown in FIG. 6 which shows a particular embodiment of patterned surface elements in the form of a plurality of raised elements.

FIG. 22 is cross section 22-22 of the patterned surface elements shown in FIG. 21.

FIG. 23 is an enlarged partial back view of the particular embodiment of the inventive intraocular implant in FIG. 6 which shows a particular embodiment of the patterned surface elements in the form of a plurality of recessed elements.

FIG. 24 is cross section 24-24 of the patterned surface elements shown in FIG. 23.

FIG. 31 is an enlarged partial front view of the particular embodiment of the inventive intraocular implant shown in FIG. 6 which shows another particular embodiment of the patterned surface elements.

FIG. 32 is cross section 32-32 of the patterned surface elements shown in FIG. 31.

FIG. 33 is an enlarged partial front view of the particular embodiment of the inventive intraocular implant shown in FIG. 6 which shows another particular embodiment of the patterned surface elements.

FIG. 34 is cross section 34-34 of the patterned surface elements shown in FIG. 33.

FIG. 35 is a front view of a particular embodiment of the inventive intraocular implant which further provides one or more boundary recess elements.

FIG. 36 is a front view of a particular embodiment of the inventive intraocular implant which includes both radial slit elements originating from the aperture element and boundary recess elements which periodically interrupt the outer boundary.

FIG. 37 is a perspective view of a plurality of an embodiment of the inventive intraocular implant which can be stacked front to back.

FIG. 38 is a perspective view of an embodiment of the inventive intraocular implant which further provides radial capillary elements.

FIG. 39 is a perspective view of an embodiment of the inventive intraocular implant which further provides corrugate elements.

FIG. 40 shows an embodiment of the intraocular implant held by forceps for implantation into an eye having the natural lens removed.

FIG. 41 is top view of the pseudophakic eye having the natural lens removed allowing an embodiment of the intraocular implant to be positioned on the surface the posterior capsule through an opening made in the anterior capsule.

FIG. 42 is a cross section view of the pseudophakic eye having the natural lens removed allowing an embodiment of the intraocular implant to be positioned on the surface the posterior capsule through an incision made in the anterior capsule.

V. MODE(S) FOR CARRYING OUT THE INVENTION

Figures 1, 2:
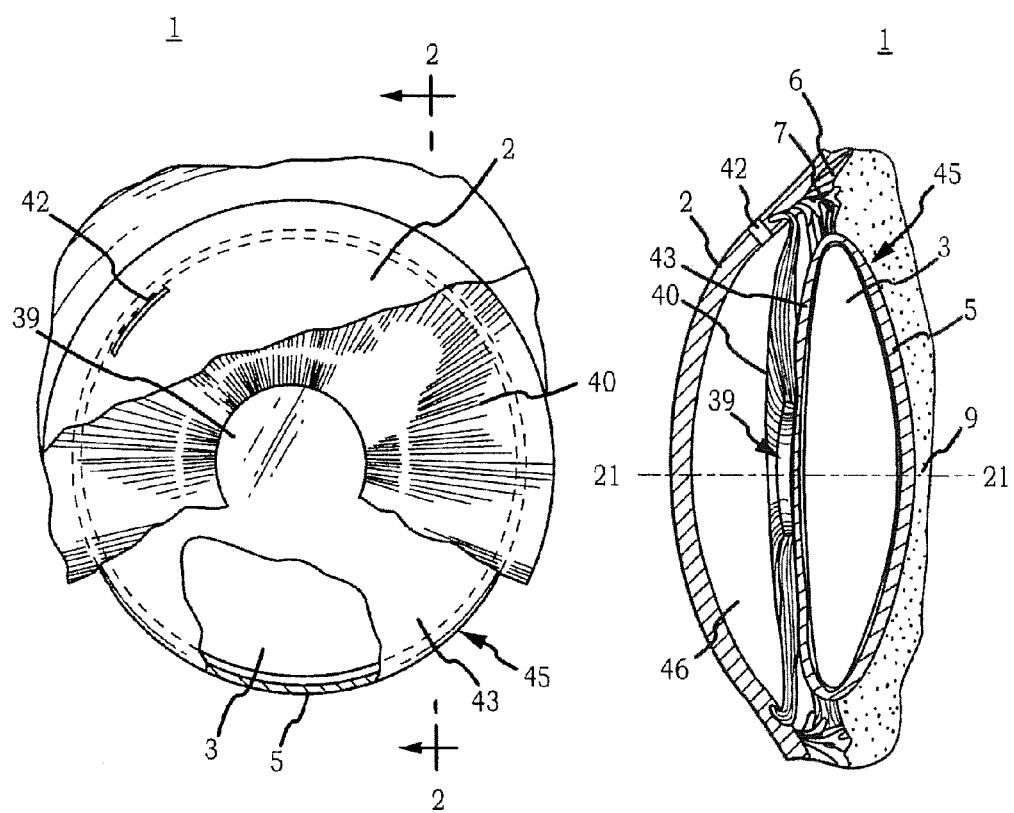
FIG. 1 is a top view of the phakic eye with the natural lens intact.
FIG. 2 is a cross section 2-2 of the phakic eye with the natural lens intact.
Figure 3:
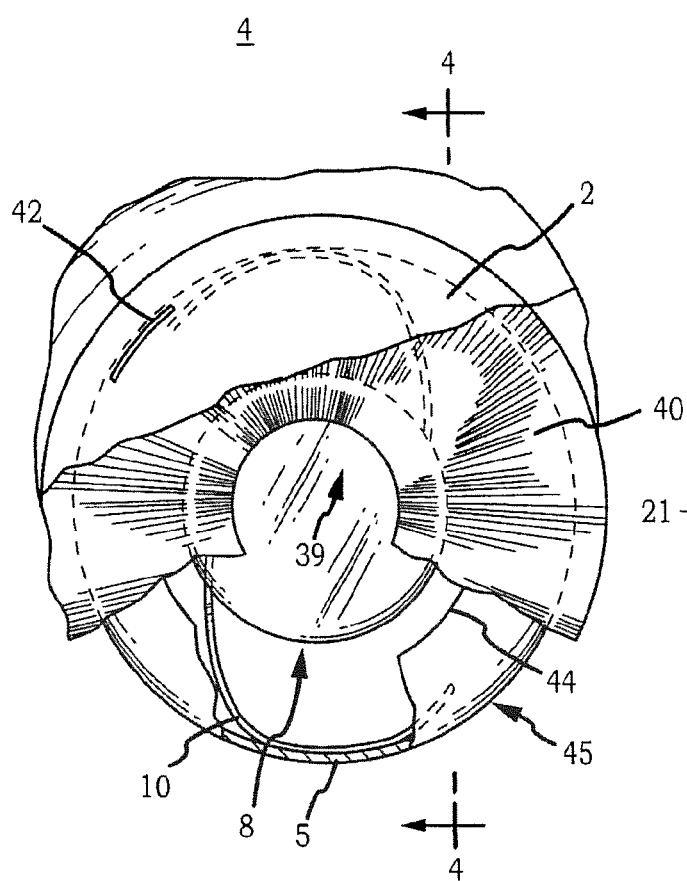
FIG. 3 is a top view of the pseudophakic eye having the natural lens replaced with an IOL.
Figure 4:
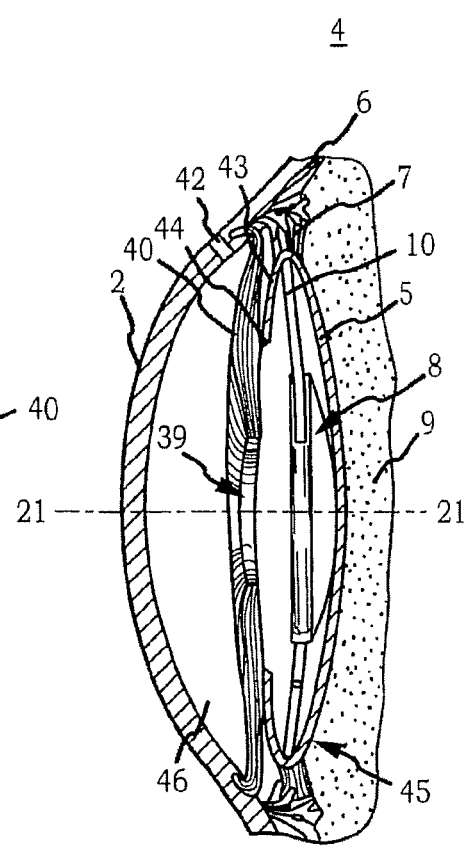
FIG. 4 is a cross section 4-4 of the pseudophakic eye having the natural lens replaced with an IOL.

Generally, an intraocular implant and methods for treating an ocular condition. In particular, an intraocular implant which implanted between an intraocular lens and the surface of the posterior capsule of the eye inhibits migration of residual lens epithelial cells after cataract surgery by providing structural barriers to reduce posterior capsule opacification of the eye.

Definitions

"A" or "an" entity refers to one or more of that entity; for example, "a polymer" refers to one or more of those compositions or at least one composition. As such, the terms "a" or "an", "one or more" and "at least one" can be used interchangeably herein. Furthermore, the language "selected from the group consisting of" refers to one or more of the elements in the list that follows, including combinations of two or more of the elements.

"About" for the purposes of the present invention means that ranges may be expressed as from "about" one particular value to "about" another particular value. When such a range is expressed, another embodiment includes from the one particular value to the other particular value. Similarly, when values are expressed as approximations, by use of the antecedent "about," it will be understood that the particular value forms another embodiment. In the context of such a numerical value or range "about" means plus or minus 10% of the numerical value or range recited or claimed.

"Active agent" for the purposes of this invention means any substance used to treat an ocular condition.

"Biocompatible" for the purposes of this invention means the ability of any material to perform the intended function of an embodiment of the invention without eliciting any undesirable local or systemic effects on the recipient and can include non-biodegradable materials such as: polyurethanes, polyisobutylene, ethylene-alpha-olefin copolymers, acrylic polymers and copolymers, vinyl halide polymers and copolymers, polyvinyl esters, polyvinylidene chloride, polyacrylonitrile, polyvinyl ketones, polyvinyl aromatics such as polystyrene, copolymers of vinyl monomers and olefins such as ethylene-methyl methacrylate copolymers, acrylonitrile-styrene copolymers, ABS resins, ethylene-vinyl acetate copolymers, polyamides such as Nylon 66 and polycaprolactone, alkyd resins, polycarbonates, polyoxyethylenes, polyimides, polyesters, epoxy resins, rayon-triacetate, cellophane, silicon rubber, silicon hydrogel, or the like, or biodegradable materials, as herein described.

"Biodegradable" for the purposes of this invention means the ability of any biocompatible material to breakdown within the physiological environment of the eye by one or more physical, chemical, or cellular processes at a rate consistent with providing structural or pharmaceutical barriers (or both) at a therapeutic level controllable by selection of a polymer or mixture of polymers (also referred to as polymeric materials), including, but not limited to: polylactide polymers (PLA), copolymers of lactic and glycolic acids (PLGA), polylactic acid-polyethylene oxide copolymers, poly($\epsilon$-caprolactone-co-L-lactic acid (PCL-LA), glycine/PLA copolymers, PLA copolymers involving polyethylene oxides (PEO), acetylated polyvinyl alcohol (PVA)/polycaprolactone copolymers, hydroxybutyrate-hydroxyvalerate copolymers, polyesters such as, but not limited to, aspartic acid and different aliphatic diols, poly(alkylene tartrates) and their copolymers with polyurethanes, polyglutamates with various ester contents and with chemically or enzymatically degradable bonds, other biodegradable nonpeptidic polyamides, amino acid polymers, polyanhydride drug carriers such as, but not limited to, poly(sebacic acid) (PSA), aliphatic-aromatic homopolymers, and poly(anhydride-co-imides), poly(phosphoesters) by matrix or pendant delivery systems, poly(phosphazenes), poly(iminocarbonate), crosslinked poly(ortho ester), hydroxylated polyester-urethanes, or the like. Hydrogels such as methylcellulose which act to release drug through polymer swelling are specifically excluded from the term.

"Intraocular" for the purposes of this invention means inside the eyeball (also referred to as an "eye") and without limitation to the forgoing the anterior chamber, the ciliary sulcus, and posterior capsule of the eye; however, specifically excluding the external surface of the eye or intracorneal or intrasclera regions of the eye.

"Localized Region" for the purposes of this invention means substantially within a localized tissue region of the eye therapeutically affected (whether structurally or pharmaceutically) by implantation of embodiments of an intraocular implant.

"Ocular condition" for the purposes of this invention means a disease, ailment or condition which affects or involves the eye or any one of the parts or regions of the eye, such as PCO. The eye includes the eyeball and the tissues and fluids which constitute the eyeball, the periocular muscles (such as the oblique and rectus muscles) and the portion of the optic nerve which is within or adjacent to the eyeball.

"Posterior ocular condition" for the purposes of this invention means a disease, ailment or condition which affects or involves a posterior ocular region or site such as the choroid or sclera (in a position posterior to a plane through the posterior wall of the lens capsule), vitreous, vitreous chamber, retina, optic nerve (i.e. the optic disc), and blood vessels and nerve which vascularize or innervate a posterior ocular region or site.

"Suitable for implantation" for the purposes of this invention means with regard to embodiments of the intraocular implant dimensions which allow insertion or implantation without causing excessive tissue damage.

"Therapeutic level" for the purposes of this invention means an amount or a concentration of an active agent that has been locally delivered to an ocular region that is appropriate to reduce, inhibit, or prevent a symptom of an ocular condition.

Now generally referring to FIGS. 5-39, particular embodiments of the inventive intraocular implant (11) can provide a biocompatible flexible membrane or a biocompatible biodegradable flexible membrane (also generally referred to as a "flexible membrane" (12)) having an outer boundary (13) configured to allow the intraocular implant (11) to locate in the concavity of the posterior capsule (5) of the pseudophakic eye (4), or other localized region inside the eye such as the ciliary sulcus or anterior chamber (46) depending on the application. As a non-limiting example, the intraocular implant (11) can be located in the posterior capsule (5) for the purpose of isolating the surface of the posterior capsule (5) from migration of residual LECs after cataract surgery, or reducing or preventing the migration of residual LECs between the surface of an IOL (8) implanted in the lens capsule (45) and the surface of the posterior capsule (5).

Intraocular implants (11) suitable for implantation can provide a flexible membrane (12) having an outer boundary (13) which as a non-limiting example defines a circular area having a diameter in a range of about 9 millimeters ("mm") and about 15 mm depending on the recipient; however, the invention is not so limited, and the outer boundary (13) can define a substantially circular, ovoid, or other configuration of the outer boundary (13) suitable for implantation into the concavity of the posterior capsule (5) of the pseudophakic eye (4), or other localized region inside the eye.

Figure 17:
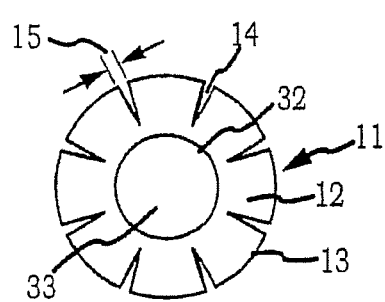
FIG. 17 is a front view of a particular embodiment of the inventive intraocular implant which further provides radial slit elements originating at the outer boundary.
Figure 18:
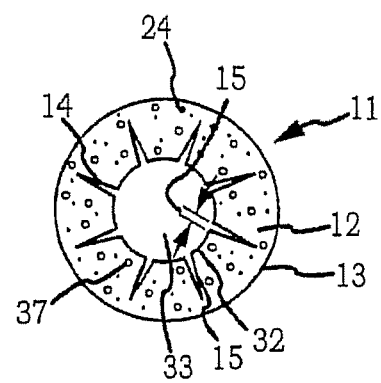
FIG. 18 is a front view of a particular embodiment of the inventive intraocular implant which further provides radial slit elements originating at the aperture element.

Now referring primarily to FIG. 17, particular embodiments of the flexible membrane (12) can further include one or more radial slit elements (14) cut through the thickness of the flexible membrane with the radial slit elements (14) originating at the outer boundary (13) cut a distance radially toward the center of the flexible membrane (12). The one or more radial slit elements (14) can have sufficient length and width to allow the flexible membrane (12) to conform to a greater extent with the concavity of the posterior capsule (5)

of the pseudophakic eye (4) or other localized region inside the eye. As one non-limiting example, the radial slit elements (14) can provide an opening in the flexible membrane (12) having a greater slit width (15) at the outer boundary (13) of the flexible membrane (12) than proximate the center of the flexible membrane (12). As a non-limiting example, the flexible membrane (12) when received by the concavity of the posterior capsule (5) can deform to reduce the slit width (15) at the outer boundary (13) of the flexible membrane (12).

Now referring primarily to FIGS. 35 and 36, particular embodiments of the flexible membrane can further provide one or more boundary recess elements (16) located along the outer boundary (13) of the flexible membrane (12). The outer boundary (13) of the flexible membrane (12) can be interrupted once or periodically to provide one or more of the recess elements (16) which can be configured, for example, as semicircular notches, triangular notches, indents, or the like which can function to allow added flexure to more readily locate the flexible membrane in the posterior capsule of the eye (or other localized region), as above described, or can function to reduce sequestration of peripheral cortical material during the final irrigation and aspiration steps in cataract surgery.

With respect to the particular embodiments of the intraocular implant shown in FIGS. 5-39 and in particular referring to FIGS. 5, 9, and 10 as a non-limiting example, the flexible membrane (12) can have a thickness (17) disposed between a front surface (18) and a back surface (19) (also referred to as "a first side" and "a second side" or "opposed sides"). As to particular embodiments of the intraocular implant (11), the front surface (18) and the back surface (19) can be disposed in substantially parallel opposed relation providing a relatively uniform thickness of the intraocular implant (11) in a range of about 5 microns ("μm") and about 400 μm, as shown by the non-limiting cross section shown in the non-limiting example of FIG. 9. Particular embodiments of the intraocular implant, can have a uniform thickness (17) in a range selected from the group including: about 5 μm and about 100 μm, about 50 μm and about 150 μm, about 100 μm and about 200 μm, about 150 μm and about 250 μm, about 200 μm and about 300 μm, about 250 μm and 300 μm, 300 μm and about 400 μm, and about 350 μm and about 400 μm. As to particular embodiments, the edge (80) at the outer boundary (13) of the intraocular implant (11) can be configured to intersect each of the front surface (18) and the back surface (19) at substantially right angles as shown in FIG. 9. Depending upon the thickness (17) of the intraocular implant (11), the optical power of the IOL (8) can be adjusted if necessary. However, embodiments of the intraocular implant are not limited to having a uniform thickness (17) and certain embodiments of the intraocular implant (11) can provide a flexible membrane (12) thinner proximate the center and thicker proximate the outer boundary (13) or can provide a flexible membrane thicker proximate the center and thinner at the edges depending upon the application. As another non-limiting example, the thickness (17) of the flexible membrane (12) may be thinner in the center to align with the visual axis of the pseudophakic eye (4) to increase visual acuity or promote directional biodegradation of the intraocular implant (11) from the center toward the outer boundary (13).

Now referring primarily to FIGS. 6, 10, 11, 12, and 13 as non-limiting examples, the intraocular implant can further include, an annular member (74) joined about, or to the front surface (18), of the intraocular implant (11). The surface of the edge (80) of the annular member (74) can define the outer boundary (13) of the intraocular implant (11). The outside surface of the edge (80) can intersect the back surface (19) of the flexible membrane (12) at an angle (78) which upon contact with the surface of the posterior capsule (5) can provide a barrier or impede migration of LECs toward the center of the intraocular implant (11). While the angle of the intersection (78) of the outside surface of the edge (80) with the back surface (19) of the intraocular implant (11) can be substantially a right angle; the invention is not so limited, and embodiments with an angle of intersection between the outside surface of the edge (80) with the back surface (19) of between about 90 degrees and about 120 degrees but retains a sharp corner can be suitable.

As to particular embodiments which include the annular member (74), the edge (80) can have a height (75) substantially greater than the thickness (17) of the flexible membrane (12). The height (75) of the edge (80) can be within the range of about 10 μm and about 1500 μm depending upon the application. As a non-limiting example, the thickness (17) of the flexible membrane (12) can be in the range of about 50 μm and about 300 μm while the annular member (74) can provide an edge (80) having a height (75) in the range of about 300 μm and about 1500 μm; however, the invention is not so limited, and the height (75) of the edge (80) as to particular embodiments can fall outside of the range depending on the application.

Figure 44:
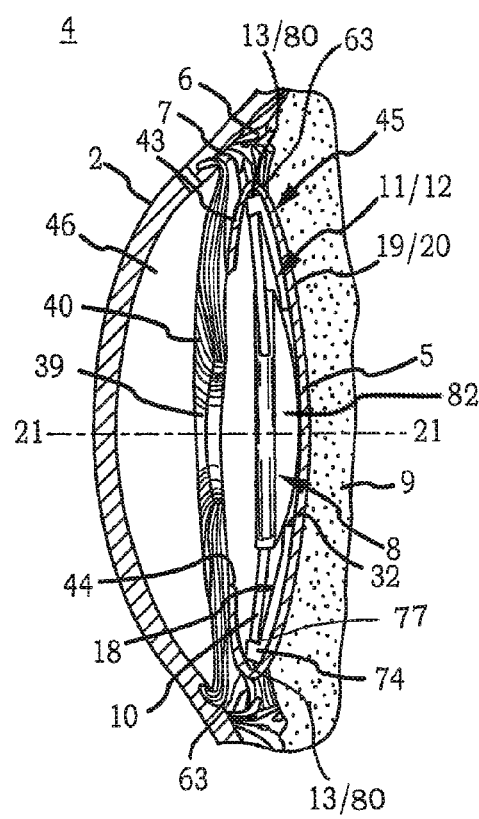
FIG. 44 is a cross section view of the pseudophakic eye having the intraocular implant of FIG. 6 positioned between the surface the posterior capsule and the implanted IOL.

Now referring primarily to FIG. 44 the height (75) of the edge (80) of he annular member (74) can be sufficiently greater than the thickness (17) of the flexible membrane (12) to provide an inside surface (77) of the annular member (74) having sufficient height (79) to engage the haptics (10) of the IOL (8) engaged with the front surface (18) of the intraocular implant (11).

Figure 45:
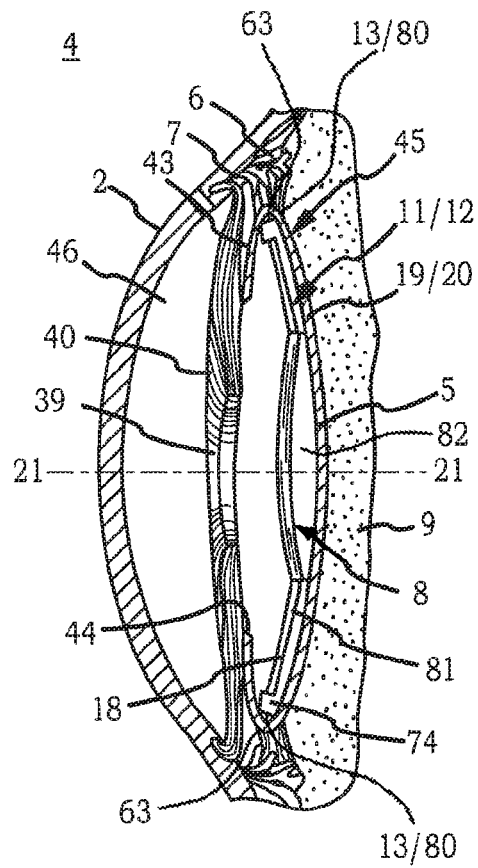
FIG. 45 is a cross section view of the pseudophakic eye having the intraocular implant of FIG. 12 positioned on the surface of the posterior capsule.
Figure 46:
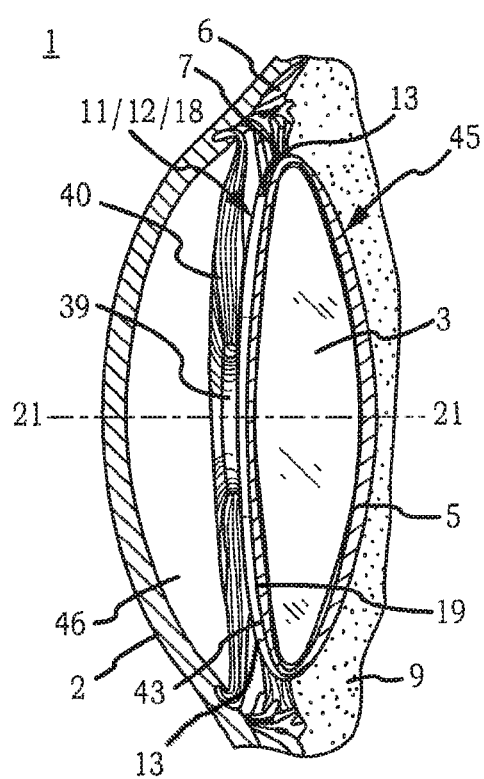
FIG. 46 is a cross section view of the phakic eye having the intraocular implant of FIG. 9 positioned between the iris and the natural crystalline lens of the eye.

Now referring primarily to FIGS. 12, 13 and 45, while embodiments of the inventive intraocular implant (11) shown in FIGS. 5 through 7, 17 through 20, 35 through 39 and 43 and 44 can be separate from the IOL (8); the invention is not so limited, and particular embodiments of the intraocular implant can be joined, coupled, or otherwise made one piece with the IOL (8), or elements of the intraocular implant (11) (such as the patterned surface elements) can be incorporated into IOL (8) such that the IOL (8) and those incorporated elements can be provided as a one piece IOL (8). The particular embodiment shown in FIGS. 12 and 13, shows the IOL (8), the flexible membrane (12) and the annular member (74) formed as one piece (the haptics (10) being omitted from the embodiment). The flexible membrane (12) can be joined about the circumference of the IOL. The flexible membrane (12) can radially extend outwardly to terminate in the edge (80) of the annular member (74). The dimensional relations of the flexible member (12) and the annular member (74) can be as above-described. A plurality of radial struts (81) can be coupled to the front surface (18) of the intraocular implant (11) between the circumference of the IOL (8) and the inside surface (77) of the annular member (74) having dimensional relations sufficient to maintain the front surface (18) and the back surface (19) of the flexible membrane (12) and the annular member (74) in proper relation to the a pseudophakic eye (4) upon implantation as shown in the non-limiting example of FIG. 42. Accordingly, the surgical technique described below can include the steps of implanting into the lens capsule (45) the IOL (8) joined, coupled or otherwise made one piece with to the intraocular implant (11) or elements thereof.

Now referring primarily to FIGS. 6 through 8, FIGS. 12 through 16, and FIGS. 21 through 34, particular embodiments of the intraocular implant (11), can provide patterned surface elements (20) coupled to the back surface (19) of the intraocular implant (11). The patterned surface elements (20) can be adapted to engage the surface of the posterior capsule (5) to reduce travel of the intraocular implant (11) or maintain the alignment of the center of the intraocular implant (11) with the visual axis of the eye (21). The patterned surface elements (20) can provide an irregular or uniform pattern, texture, or roughness sufficient to fix or reduce travel of the intraocular implant (11) in the posterior capsule (5).

As to certain embodiments of the intraocular implant (11) the patterned surface elements (20) can also provide pockets which function to provide a localized space to deliver or sequester an amount of an active agent (24). The patterned surface elements can be variously configured to deliver or sequester an active agent (24) depending on the application. The pattern surface elements (20) can be one piece with the flexible membrane (12) or can be applied to the flexible membrane (12) as a pattern surface element layer.

As to certain embodiments of the intraocular implant (11), whether in the form of the inventive implant as shown in the examples of FIGS. 5 through 11 which can be combined with otherwise made one piece with the IOL (8) or in the form of the various embodiments of a one-piece IOL (8) as shown in the examples of FIGS. 12 through 16, patterned surface elements (20) can be coupled to the front surface (18) or the back surface (19) of the intraocular implant (11) to provide an irregular or uniform pattern, texture, roughness, or dimensional relations sufficient to inhibit migration of cells, such as residual lens epithelial cells, after cataract surgery by providing structural barriers as shown in the examples of FIGS. 21 through 34. The patterned surface elements (20) can be configured to provide a sufficient structural barrier to the migration of residual lens epithelial cells to eliminate, substantially eliminate or reduce posterior capsule (5) opacification of the pseudophakic eye (4). As to certain embodiments, the intraocular implant (11) can include the IOL (8) comprising an intraocular lens optic (82) and an intraocular lens haptic (83) with patterned surface elements (20) coupled to at least a part of said IOL (8) while maintaining a the visual axis (21) through the intraocular lens optic (82), the patterned surface elements (20) having dimensional relations adapted to inhibit migration of cells between the IOL (8) and the surface of said posterior capsule (5) of the eye.

In general, the patterned surface elements (20) can include a plurality of raised elements (47) or a plurality of recessed elements (69) which project outwardly or recess inwardly from the back surface (19) or the front surface (18) of the biocompatible flexible membrane (12) of the intraocular implant (11) in spaced apart relation to one another.

As to certain embodiments, the plurality of raised elements (47) can be bounded by a corresponding plurality of channels (48) which form a pattern over the entirety or over a portion of the back surface (19) or the front surface (18), or both the front surface (18) and the back surface (19) of the biocompatible flexible membrane (12) of the intraocular implant (11). The plurality of raised elements (47) can be produced from one or more of the biocompatible or biodegradable materials, as above described, which as to certain embodiments can be a material different than used to form the biocompatible or biocompatible biodegradable flexible membrane (12). The top surface (49) of each of the plurality of raised elements (47) can be generally flat or planar having a surface area sufficiently small to reduce or prevent adhesion or migration of residual lens epithelial cells across the plurality of raised elements (47) and each of the plurality of channels (48) can be sufficiently small to reduce or prevent migration or adhesion between the plurality of raised elements (47). The plurality of raised elements (47) can be disposed in spaced apart relation on the back surface (19) or the front surface (18), or both, of the biocompatible or biocompatible biodegradable flexible membrane (12) to dispose the plurality of channels in a non-linear path (67) inwardly approaching the center of the intraocular implant (11). The various embodiments of the patterned surface elements (20) can occur only on the back surface (19), only on the front surface (18) or can occur on both the back surface (19) and on the front surface (18).

Embodiments of the top surface (49) of each of the plurality of raised elements can have a lesser dimension between two sidewalls (50)(see for example FIG. 13) in the range of about 500 nanometers and about 4 micrometers. Depending upon the application, the lesser dimension can be selected from the group including: about 400 nanometers and about 1 micrometer, about 500 nanometers and about 1.5 micrometers, 1 micrometer an about 2.0 micrometers, 1.5 micrometers and about 2.5 micrometers, 2.0 micrometers and about 3.0 micrometers, 2.5 micrometers and about 3.5 micrometers, 3.0 micrometers and about 4.0 micrometers, and 3.5 micrometers and about 4.0 micrometers, or combinations thereof.

Understandably, the top surface (49) as between two or more of the plurality of raised elements (47) can be configured in substantially similar configuration and similar in dimensional relations or as between two or more of the plurality of raised elements (47) can be substantially different in configuration or irregular in dimensional relations. The lesser dimension can as to particular embodiments relate to the width of one of the plurality of raised elements (47) and the greater dimension as to particular embodiments can relate to a length of one of the plurality of raised elements (47). However, the invention is not so limited; and numerous and varied embodiments can be produced in which the top surface has an irregular surface area, or may be substantially circular or can be a regular polygon, or the like, which do not afford a distinction between width and length. Accordingly, the above dimensions afford guidance sufficient for the person of ordinary skill in the art to provide a plurality of raised elements (49) in spaced apart relation having a wide variety of configurations useful in inhibiting adhesion and migration of cells toward the center of the intraocular implant (11).

The sidewalls (50) of each of the plurality of raised elements (47) can be generally vertical to the surface of the intraocular implant (11) when the biocompatible flexible membrane (12) is disposed in a generally flat condition. The sidewalls (50) can have a sidewall height (51) in the range of about 400 nanometers and about 6 micrometers. Depending upon the application, the sidewall height (51) can be selected from the group including: about 400 nanometers and about 1 micrometer, about 500 nanometers and about 1.5 micrometers, 1 micrometer an about 2.0 micrometers, 1.5 micrometers and about 2.5 micrometers, 2.0 micrometers and about 3.0 micrometers, 2.5 micrometers and about 3.5 micrometers, 3.0 micrometers and about 4.0 micrometers, 3.5 micrometers and about 4.5 micrometers, 4.0 micrometers and about 5.0 micrometers, about 4.5 micrometers and about 5.5 micrometers, and about 5.0 micrometers and about 6.0 micrometers, or combinations thereof.

Each of the plurality of channels (48) defined by opposed sidewalls (50) can have a channel width (61) in the range of about 100 nanometers and about 2.5 micrometers. Depending upon the application, a suitable channel width (61) (see for example FIG. 17) can be selected from the group including: 100 nanometers and about 300 nanometers, about 200 nanometers and about 400 nanometers, about 300 nanometers and about 500 nanometers, about 400 nanometers and about 600 nanometers, about 500 nanometers and about 700 nanometers, about 600 nanometers and about 800 nanometers, about 700 nanometers and about 900 nanometers about 800 nanometers and about 1 micrometer, about 900 nanometers and about 1.1 micrometer, 1 micrometer an about 1.2 micrometer, 1.1 micrometer and about 1.3 micrometer, 1.2 micrometer and about 1.4 micrometer, 1.3 micrometer and about 1.5 micrometers, 1.4 micrometer and about 1.6 micrometer, 1.5 micrometer and about 1.7 micrometer, 1.6 micrometer and about 1.8 micrometer, 1.7 micrometer and about 1.9 micrometer, and about 1.8 micrometer and about 2 micrometer, or combinations thereof.

Now referring primarily to FIGS. 21 through 34, which provide non-limiting examples of raised elements (20) or recessed elements (69) which can be useful in inhibiting the migration of cells between the back surface (19) of the biocompatible flexible membrane (12) and the surface of the posterior capsule (5) of the a pseudophakic eye (4) or can be useful in inhibiting the migration of cells between the front surface (18) and an implanted intraocular lens (8).

As to the non-limiting example of FIGS. 21-26, the patterned surface elements (20) can have the topography (or reverse topography) of a shark's skin as described in U.S. Pat. No. 7,650,848, hereby incorporated by reference herein to the extent that that the description does not conflict with the express description of embodiments of the patterned surface elements (20). The topography of the shark skin can be scaled to inhibit adhesion and migration of residual lens epithelial cells between the back surface (19) of the intraocular implant (11) and the surface of the posterior capsule (5) of the pseudophakic eye (4). As one non-limiting example, the topography of the shark skin can be characterized by a plurality of repeating diamond patterns (52) each consisting of a plurality of raised elements (47) including seven bar elements (53). The diamond pattern (52) can have an overall diamond length (68) in the range of about 15 micrometers and about 25 micrometers. Each of the seven bar elements (53) can have a bar width (60) in the range of about 1 micrometer and about 2.5 micrometers and having a corresponding one of a plurality of channels (48) each having channel width (61) of about 400 nanometers and about 2 micrometer. The seven bar elements (53) can have a bar length (54) in the range of about 4 micrometers and about 20 micrometers. The height of the side wall (50) for each of the seven bar elements (53) can be in the range of about 1 micrometer and about 5 micrometers.

Now referring primarily to FIGS. 23-24, particular non-limiting examples of the patterned surface elements (20) can take the form of the topography of a shark's skin as above described; however, the plurality of raised elements (47) and plurality of channel (48) can be replaced by a corresponding plurality of recessed elements (69) having corresponding plurality of bottom surfaces (70) and spacer elements (71) having a corresponding spacer width (73) to form substantially the same pattern having substantially the same dimensional relations as above described. Again, any of patterned surface elements (20) described herein as a plurality of raised elements (47) and a corresponding plurality of channel elements (48) can take the constructional form of a plurality of recessed elements (70) and a plurality of spacer elements (71) having substantially the same or similar pattern or dimensional relations in the ranges above described.

Figure 20:
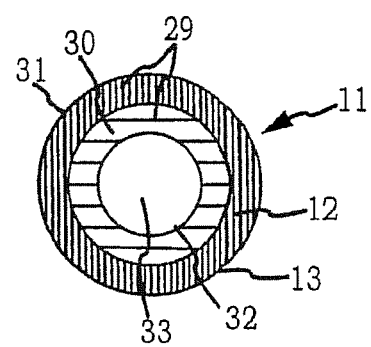
FIG. 20 is a front view of a particular embodiment of the inventive intraocular implant which further provides two more flexible membrane zones.
Figures 25, 26:
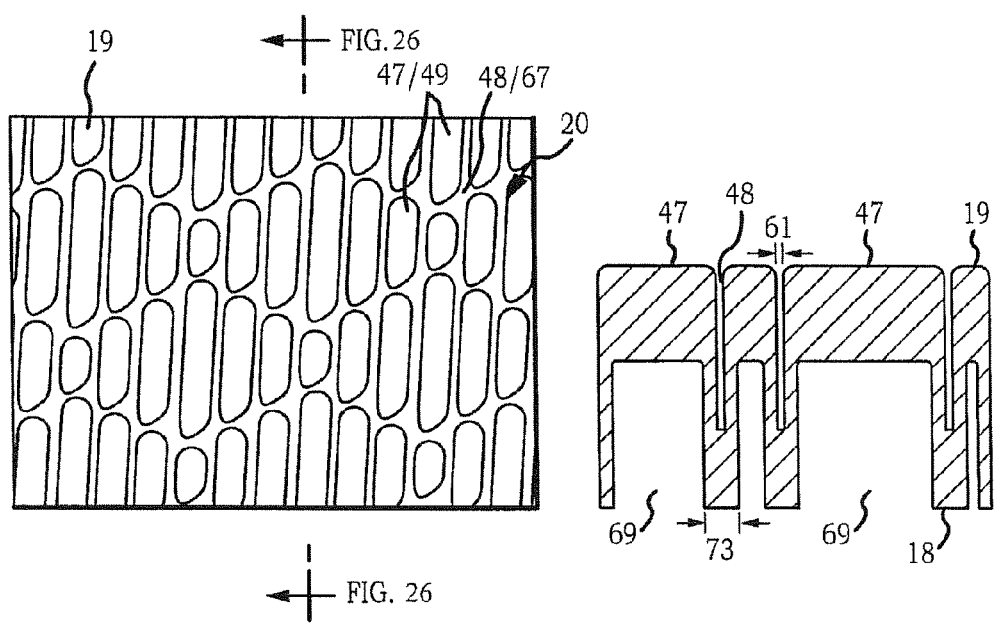
FIG. 25 is an enlarged partial back view of the particular embodiment of the inventive intraocular implant in FIG. 6 which shows a particular embodiment of the patterned surface elements in the form of a plurality of raised elements on the back surface and a plurality of recessed elements on the front surface.
FIG. 26 is cross section 26-26 of the patterned surface elements shown in FIG. 25 which shows a plurality of raised elements on the back surface of a particular embodiment of the inventive intraocular implant and a plurality of recessed elements on the front surface of the inventive intraocular implant.

Now referring primarily to FIGS. 25 and 26, particular embodiments of the patterned surface elements (20) can take the form of a plurality of raised elements (47) on one side of the biocompatible flexible membrane (12) and a plurality of recessed elements (69) on the opposed side of the biocompatible flexible membrane (12). While FIGS. 20 and 21 show a plurality of raised elements (47) on the back side (19) of the biocompatible flexible membrane (12) and a plurality of recessed elements (69) on the front side (18) of the biocompatible flexible membrane (12); the invention is not so limited, and the a plurality of recessed elements (69) can occur on the back side (19) while the plurality of raised elements can occur on the front side (18) of the biocompatible flexible membrane (12).

Figures 27, 28:
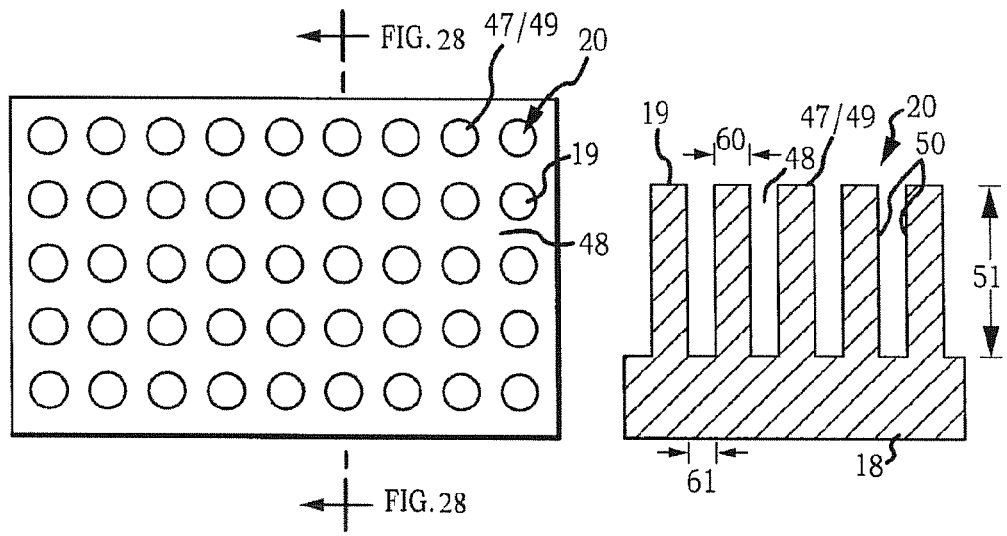
FIG. 27 is an enlarged partial front view of the particular embodiment of the inventive intraocular implant shown in FIG. 6 which shows another particular embodiment of the patterned surface elements.
FIG. 28 is cross section 28-28 of the patterned surface elements shown in FIG. 27.

Now referring primarily to FIGS. 27 and 28, particular embodiments of the patterned surface elements (20) can take the form of a plurality of raised elements (47) each having a generally cylindrical configuration in spaced apart relation of columns and rows. Each of the plurality of raised elements (47) having substantially circular top surface (49) having a diameter in the range of about 400 nanometers and about 600 nanometers and side wall (50) having a height of about 400 nanometers and about 600 nanometers. The plurality of raised elements (47) can be established on centers in the range of about 600 nanometers and about 1 micrometer affording a distance between the sidewalls (50) of between about 200 nanometers and about 400 nanometers.

Figures 29, 30:
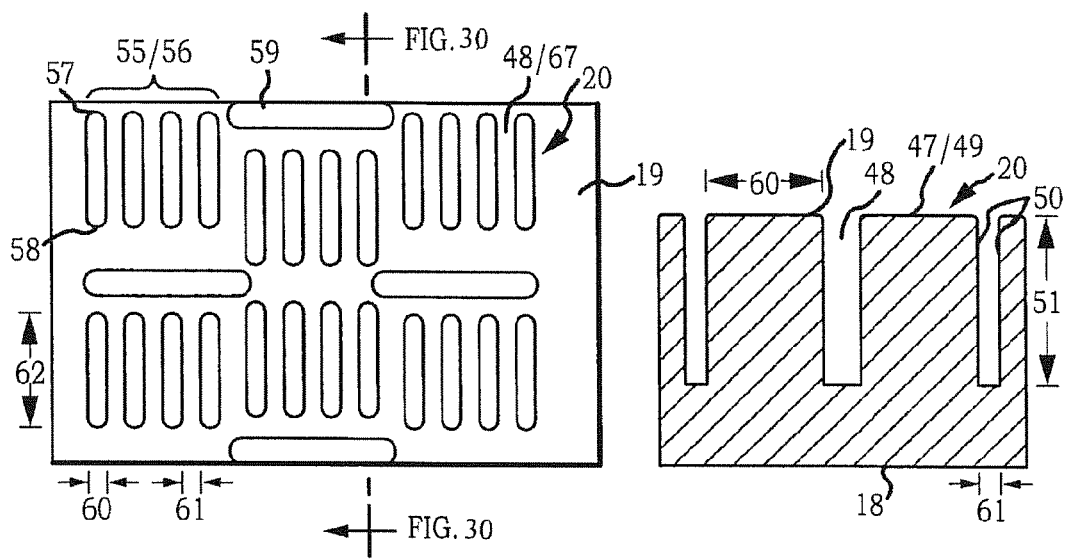
FIG. 29 is an enlarged partial front view of the particular embodiment of the inventive intraocular implant shown in FIG. 6 which shows another particular embodiment of the patterned surface elements.
FIG. 30 is cross section 30-30 of the patterned surface elements shown in FIG. 29.

Now referring primarily to FIGS. 29 and 30, particular embodiments of the patterned surface elements (20) can take the form of a plurality of raised elements (47) in the form of a plurality of repeating bar patterns (55) each characterized by four bar elements (56) of substantially equal length in spaced apart generally parallel relation having corresponding aligned first ends (57) and aligned second ends (58) with a cross bar (59) disposed in generally perpendicular relation a distance from the aligned first ends (57) or aligned second ends (58) of the four bar elements (56). Each of the four bar elements (56) can have a width (60) in the range of about 2 micrometers and about 5 micrometers and having a corresponding one of a plurality of channels (48) each having width (61) of about 400 nanometers and about 1 micrometer. The four bar elements (56) can each have a length (62) in the range of about 4 micrometers and about 20 micrometers. The height of the side wall (50) of each of the four bar elements (56) can be in the range of about 1 micrometer and about 3 micrometers. The cross bar (59) can be disposed a distance from the aligned first ends (57) or aligned second ends (58) of the four bar elements (56) (or may alternate between the aligned first ends (57) and aligned second ends (58) as the pattern repeats) in the range of about 400 nanometers and about 1 micrometer. The length of the cross bar (59) can be sufficient to span the distance of the spaced apart relation of the four bar elements (56). The cross bar (59) having dimensional relations otherwise similar to the four bar elements (56).

Now referring primarily to FIGS. 31 and 32, embodiments of the patterned surface elements (20) can take the form of a plurality of raised elements (47) each having a top surface (20) of generally hexagonal configuration in regular spaced apart tessellation. Each of the hexagonal top surface (49) can have a width (60) in the range of about 400 nanometers and about 600 nanometers and side wall (50) having a height of about 400 nanometers and about 600 nanometers. The corresponding plurality of channels (48) can have a width (61) of about 100 nanometers and about 200 nanometers between each of the plurality of raised elements (47).

Now referring primarily to FIGS. 33 and 34, embodiments of the patterned surface elements (20) can take the form of a plurality of raised elements (47) in the form of a plurality of bar elements (65) in a herringbone pattern. Each of the plurality of bar elements (65) can be of substantially equal length in the range of about 4 micrometers and about 20 micrometers and having a width (61) in the range of about 2 micrometers and about 5 micrometers. The height of the side walls (51) of each of the plurality of bar elements (65) can be in the range of about 1 micrometer and about 3 micrometers. The corresponding plurality of channels (48) between the plurality of bar elements (65) can have a channel width (60) of about 400 nanometers and about 1 micrometer.

Figure 19:
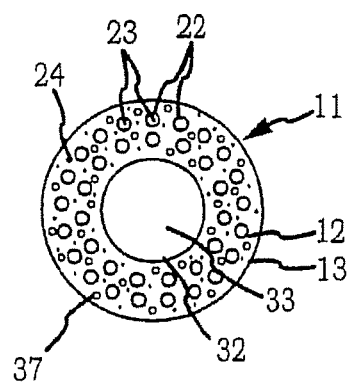
FIG. 19 is a front view of a particular embodiment of the inventive intraocular implant which further provides perforation elements.

Now referring primarily to FIG. 19, certain embodiments of the flexible membrane (12) can further include one or more perforation elements (22) which provide a corresponding one or more perforation openings (23) which communicate between the front surface (18) and the back surface (19) of the flexible membrane (12) for the purpose of increasing rate of biodegradation of the flexible membrane (12) or control release rate of an active agent (24). The active agent (24) (shown for example in FIGS. 9, 10 and 13 as a stipple pattern) is not intended to be limited to those particular embodiments of the intraocular implant (11) or limit the active agent (24) to any particular composition, particle size, or amount.

Now referring primarily to FIG. 37, certain embodiments of the flexible membrane (12) can further provide two or more flexible membrane layers (25). The two or more membrane layers (25) can take the form of a first flexible membrane layer (26) and a second flexible membrane layer (27) or additional flexible membrane layers (28) extruded as a single piece, coupled together as one unit, or stacked front to back (whether single piece, coupled or stacked the term "coupled" may be used to refer to the association of a plurality of flexible membrane layers). Each of the first flexible membrane layer (26) and the second flexible membrane layer (27) or additional flexible layers (28) can be generated from the same or different biocompatible biodegradable materials. As a non-limiting example, in an embodiment of the invention for the treatment of PCO, the first flexible membrane layer (26) can be made of a biocompatible or biocompatible biodegradable material which can have the back surface (19) disposed adjacent the surface of the posterior capsule (5) to provide both a structural barrier to the migration of LECs to the surface of the posterior capsule but to further function as a pharmaceutical barrier which inhibits proliferation or kills LECs by the substantially continuous release of an active agent (24) such as alkylphosphocholine at a rate which provides a therapeutic level, such as a localized concentration of about 1.0 millimolar ("mM") for a period of at least five days to inhibit or prevent PCO. The front surface (18) of the first flexible membrane layer (26) can be coupled adjacent the back surface (19) of the second flexible membrane layer (27) (for example by melt co-extrusion) produced from the same or different biocompatible biodegradable material and the front surface (18) of the second flexible membrane layer (27) can be disposed toward an IOL (8) implanted into the posterior capsule (5) to provide a structural barrier to migration of LECs toward the surface of the posterior capsule and can further function as a pharmaceutical barrier which inhibits proliferation or kills LECs by the substantially continuous release of the same active agent (24) (such as an alkylphosphocholine) or a different active agent (24) such as mitomycin-C at a therapeutic level, such as a localized concentration of about 0.04 mg/mL, for a period of at least about five days to inhibit or prevent PCO. Thus, by configuring the layers in different combinations the rate of release of various active agents can be adjusted depending on the application.

Now referring primarily to FIG. 20, two or more flexible membrane zones (29) can be established with each flexible membrane zone (29) generated from a particular flexible membrane material. As to certain embodiments, the two or more flexible membrane zones (29) can be established as concentric regions with a first annular zone (30) surrounded by a second annular zone (31). The first annular zone (30) can be of different biocompatible or biocompatible biodegradable material then the second annular zone (31). For example, the first annular zone (30) can provide a biocompatible biodegradable material selected for a greater rate of biodegradation or active agent (24) release (or both) relative to the second annular zone (31) which can provide a biocompatible biodegradable material selected for a lesser rate of biodegradation or active agent (24) release (or both). In that configuration of the inventive intraocular implant (11), the prominent function of the first annular zone (30) can be to provide a pharmaceutical barrier or treatment of an ocular disorder, while the prominent function of the second annular zone (31) can be to provide a structural barrier or treatment of an ocular disorder. In particular embodiments of the inventive intraocular implant for the inhibition of PCO, the first annular zone can be made of the biocompatible biodegradable material poly (lactide-co-glycolide) having an active agent (24) such as alkylphosphocholine dispersed substantially uniformly through out which can provide a pharmaceutical barrier to the proliferation of LECs on the surface of the posterior capsule (5) to inhibit or prevent PCO by release of a therapeutic level of alkylphosphocholine of about 1.0 mM for a period of at least about five days. The first annular zone (30) can substantially biodegrade in the entirety in a period of about five days to about ten days. The second annular zone can be made of the same biocompatible biodegradable material having the same or different active agent (24) dispersed substantially uniformly throughout to provide both a structural barrier to inhibit migration of LECs toward to the surface of the posterior capsule and can provide a pharmaceutical barrier by release of the same or different active agent (24) such as alkylphosphocholine at a therapeutic level or provide a localized concentration of about 1.0 mM for a period of at least twenty days to inhibit or prevent PCO.

Again referring generally to FIGS. 5 through 11, 17 through 20, and 35 through 36, particular embodiments of the inventive intraocular implant (11) can further include an aperture element (32) having a passage opening (33) sufficiently large to align with the visual axis of the eye (21) to provide a line of sight which passes through the intraocular implant (11) or the first annular zone (30) or the second annular zone (31).

While the aperture element (32) shown in FIGS. 5 through 11, 17 through 20, and 35 through 39 define a substantially circular passage opening having a diameter in the range of about 1.5 mm and about 9 mm depending upon the application and the recipient; the invention is not so limited and certain embodiments of the inventive intraocular implant (11) can provide an aperture element (32) which defines an oval, square, triangle, or other configuration of passage opening (33) sufficient to provide a line of sight which passes through the intraocular implant (11). As to those embodiments of the invention which are utilized with an intraocular optical implant, such as an IOL as further described herein, the passage opening (33) can be dimensioned in relation to the intraocular optical implant to avoid reduction in the field of vision provided by the intraocular optical implant or to avoid a reduction in clarity of vision within visual field. Alternately, in those embodiments of the invention in which the passage opening (33) has insufficient dimension to avoid overlaying all or part of the visual field afforded by the intraocular optical implant, embodiments of the intraocular implant (11) can be further configured to provide an optical element of sufficient clarity so as not to substantially effect vision within the visual field afforded by an intraocular implant (11).

Now referring specifically to FIGS. 18, and 36 through 38, the aperture element (33) can further include one or more radial slit element's (14) each originating at the aperture element (33) and terminating at a distance from the outer boundary (13) of the flexible membrane (12). The one or more radial slit elements (14) can have sufficient length and width to allow the flexible membrane (12) to conform to a greater extent with the concavity of the posterior capsule (5)(or other localized region) of the eye and with respect to embodiments of the intraocular implant (11) which are biodegradable can function to promote directional biodegradation of the intraocular implant proximate the aperture element toward the outer boundary (13). Again, the radial slit elements (14) can provide one or more interruptions in the aperture element (32) which can be of lesser or greater width or length to control the rate at which the flexible membrane (12) biodegrades within the posterior capsule (5) of the eye.

Now referring primarily to FIG. 38, particular embodiments of the intraocular implant (11) can further provide radial capillaries (34) which communicate between the outer boundary (13) and the aperture element (32) of the flexible membrane (12) configured to allow or facilitate circulation of the fluid within the eye, for example, between the flexible membrane (12) and the posterior capsule (5) of the eye.

Similarly, as shown by FIG. 39, particular embodiments of the intraocular implant (11) can further provide one or more corrugate elements (35) which can be disposed in substantially linear parallel relation to generate undulations in the flexible membrane (12) sufficient when the flexible membrane (12) locates against the surface of the posterior capsule (5) (or surface of a localized region) to provide channels (36) in which the fluids of the eye can circulate.

Referring in general to FIGS. 5-39, embodiments of the intraocular implant can further include an active agent (24) (shown as stipple pattern in FIGS. 18, 19, and 36 although the invention is not so limited) mixed with or dispersed in the biodegradable polymer of the flexible membrane (12). The composition of the biodegradable polymers of the flexible membrane (12) of the intraocular implant (11) can be varied to provide a continuous or substantially continuous release of a therapeutic level of a particular active agent (24) or a particular mixture of active agents (24) effective for the ocular condition being treated. Active agents (24) that can be used include, but are not limited to (either alone or in combination): ace-inhibitors, endogenous cytokines, agents that influence the basement membrane, agents that influence the growth of endothelial or epithelial cells, adrenergic agonists or blockers, cholinergic agonists or blockers, aldose reductase inhibitors, analgesics, anesthetics, antiallergics, anti-inflammatory agents, antihypertensives, pressors, antibacterials, antivirals, antifungals, antiprotozoals, anti-infectives, antitumor agents, antimetabolites such as daunomycin, anti-angiogenic agents, tyrosine kinase inhibitors, antibiotics such as aminoglycosides such as gentamicin, kanamycin, neomycin, and vancomycin; amphenicols such as chloramphenicol; cephalosporins, such as cefazolin HCl; penicillins such as ampicillin, penicillin, carbenicillin, oxycillin, methicillin; lincosamides such as lincomycin; polypeptide antibiotics such as polymixin and bacitracin; tetracyclines such as tetracycline, minocycline, and doxycycline; quinolones such as ciprofloxacin, moxifloxacin, gatifloxacin, and levofloxacin; sulfonamides such as chloramine T; sulfones such as sulfanilic acid; anti-viral drugs such as acyclovir, gancyclovir, vidarabine, azidothymidine, dideoxyinosine, dideoxycytosine; epinephrine; isoflurphate; adriamycin; bleomycin; mitomycin; ara-C; actinomycin D; scopolamine; and the like, analgesics, such as codeine, morphine, ketorolac, naproxen, an anesthetic, lidocaine; beta.-adrenergic blocker or beta.-adrenergic agonist such as ephedrine, and epinephrine; aldose reductase inhibitor such as epalrestat, ponalrestat, sorbinil, tolrestat; antiallergic such as cromolyn, beclomethasone, dexamethasone, and flunisolide; colchicine, anihelminthic agents such as ivermectin and suramin sodium; antiamebic agents such as chloroquine and chlortetracycline; and anti-fungal agents such as amphotericin; anti-angiogenesis compounds such as anecortave acetate; retinoids such as Tazarotene, anti-glaucoma agents such as brimonidine (Alphagan and Alphagan P), acetozolamide, bimatoprost (Lumigan), timolol, mebefunolol; memantine; alpha-2 adrenergic receptor agonists; 2-methoxyestradiol; anti-neoplastics such as vinblastine, vincristine, interferons; alpha, beta and gamma., antimetabolites such as folic acid analogs, purine analogs, and pyrimidine analogs; immunosuppressants such as azathyprine, cyclosporine and mizoribine; miotic agents, such as carbachol, mydriatic agents such as atropine, etc., protease inhibitors such as aprotinin, camostat, gabexate, vasodilators such as bradykinin, epidermal growth factor, basic fibroblast growth factor, nerve growth factors, steroidal anti-inflammatory agents such as 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide; vascular endothelial growth factor inhibitors such as bevacizumab, ranibisumab, pegatanib; transforming growth factor inhibitors; fibroblast growth factor inhibitors, and any of their derivatives.

As to particular embodiments of the inventive intraocular implant the active agent (24) can be dispersed throughout the biocompatible biodegradable polymer of the flexible membrane (12) by mixing the active agent (24) into the melted biodegradable polymer and then solidifying the resulting biodegradable polymer by cooling, having the active agent (24) substantially uniformly dispersed throughout. The biodegradable polymer or mixture of biodegradable polymers can be selected to have a melting point that is below the temperature at which the active agent (24) becomes reactive or degrades. Alternatively, the active agent (24) can be dispersed throughout the biodegradable polymer by solvent casting, in which the biodegradable polymer is dissolved in a solvent, and the active agent (24) dissolved or dispersed in the solution. The solvent is then evaporated, leaving the active agent (24) in the polymeric matrix of the biodegradable material. Solvent casting requires that the biodegradable polymer be soluble in organic solvents. Alternatively, the biodegradable intraocular implant (11) can be placed in a solvent having a concentration of the active agent (24) dissolved and in which the biodegradable intraocular implant swells. Swelling of the biodegradable intraocular implant draws in an amount of the active agent (24). The solvent can then be evaporated leaving the active agent (24) within the flexible membrane (12) of the biodegradable intraocular implant (12). As to each method of dispersing the active agent (24) through out the biodegradable polymer of the flexible membrane (12), therapeutic levels of active agent (24) can be included in biocompatible biodegradable polymer to treat a particular ocular condition. The biodegradable polymer usually comprises at least about 10, at least about 20, at least about 30, at least about 40, at least about 50, at least about 60, at least about 70, at least about 80, or at least about 90 weight percent of the implant with the balance of the weight being the active agent (24) or other non-active agents (37) dispersed in the biocompatible biodegradable polymer (shown as open stipples in FIGS. 9 and 13; however, the non-active agents are not limited to these particular embodiments of the flexible membrane (12)).

Other non-active agents (37) may be included in the biocompatible biodegradable polymer formulation for a variety of purposes. For example, buffering agents and preservatives may be employed. Preservatives which may be used include, but are not limited to, sodium bisulfite, sodium bisulfate, sodium thiosulfate, benzalkonium chloride, chlorobutanol, thimerosal, phenylmercuric acetate, phenylmercuric nitrate, methylparaben, polyvinyl alcohol and phenylethyl alcohol. Examples of buffering agents that may be employed include, but are not limited to, sodium carbonate, sodium borate, sodium phosphate, sodium acetate, sodium bicarbonate, and the like, as approved by the FDA for the desired route of administration. Electrolytes such as sodium chloride and potassium chloride may also be included in the formulation.

A non-limiting example of producing biodegradable embodiments the inventive intraocular implant for treating an ocular condition such as PCO can be made by mixing an active agent (24) and biodegradable polymer to form an active agent polymer material. The active agent polymer material can be extruded or molded to form embodiments of the biocompatible biodegradable intraocular implant (11) or flexible membrane (12) having active agent release characteristics at a therapeutic level. As but one non-limiting example, the intraocular implant (11) can substantially continuously release active agent (24) to provide a localized concentration of alkylphosphocholine at therapeutic levels of about 0.5 mM to 1.5 mM for at least 5 days or release mitomycin-C to provide a localized concentration of 0.04 mg/mL, or both, for a period of at least about five days to inhibit or prevent PCO. It is to be understood that this specific example of providing an embodiment of an intraocular implant (11) for the inhibition or prevention of PCO, is not intended to be limiting, and embodiments of the intraocular implant (11) can be utilized to treat a wide range of ocular conditions including posterior ocular conditions or anterior chamber conditions of the eye.

Embodiments of the biocompatible flexible membrane (12) or the biocompatible biodegradable flexible membrane (12) can be made by a variety of methods, and while not particularly limited, examples of molding methods which can be used to form a film or sheet includes T-die molding, inflation molding, calender molding, heat press molding, spin cast molding, injection molding, cast molding, or the like.

The inventive intraocular implant (11) of a biodegradable polymer of the invention can be molded in thinner thickness in order to increase biodegradability, but its thickness can be freely adjusted to satisfy strength, flexibility and release of active agents (24) to achieve therapeutically effective levels localized to the site of implantation of the intraocular implant. Thickness of the flexible membrane can be in the range of about 5 to about 300 μm, or about 10 μm to 100 μm. Elastic modulus of the flexible can generally be 1,200 MPa or less, more preferably 600 MPa or less. Tensile strength can fall in the range of about 10 MPa to 100 MPa, more preferably in a range of 15 MPa to 70 MPa, further more preferably in a range of 20 MPa to 50 MPa.

Again referring primarily to FIGS. 1-4, as above described the most common surgical technique of cataract surgery may be ECCE (although use of the inventive intraocular implant (11) is not limited to cataract surgery or to any particular technique of cataract surgery) which involves the creation of a circular opening (44) in the anterior lens capsule (43) through which the opacified lens (3) can be removed. The remaining portion of the lens capsule (45), anchored to the ciliary body (6) through the zonular fibers (7) can be left intact. The IOL (8) can then be placed within the lens capsule (45). The IOL (8) can be acted on by zonular forces exerted on the outer circumference of the lens capsule (45) which establishes the location of the IOL (8) within the lens capsule (45). The intact posterior capsule (5) acts as a barrier to the vitreous humor (9).

Now referring primarily to FIGS. 40 through 42, following cataract extraction and cortex removal by ECCE or other surgical procedures to treat other ocular conditions, embodiments of the biocompatible or biocompatible biodegradable intraocular implant (11) can be held in forceps (38) as shown for example in FIG. 40. Embodiments of the intraocular implant (11) may also be removably fixed to the surface of a small card (41) (or intraocular implant packaging substrate) from which it can be lifted with the forceps (38) prior to insertion into the eye as shown for example in FIGS. 41 and 42. The intraocular implant (11) can be folded upon itself to reduce the apparent dimension for passage through the corneal or scleral incision (42) as well as circular opening (44) in the anterior lens capsule (43) surrounded by the pupil (39) of the iris (40), as shown in FIGS. 40-42.

Now referring specifically to FIG. 42, which provides an example of a non-limiting method, the intraocular implant (11) can be positioned within localized region of the lens capsule (45) having a front surface (18) (which can further provide patterned surface elements (20) as above described) proximate the surface or engaging the surface of the posterior capsule (5). The passage opening (33), of embodiments of the intraocular implant (11) which provide an aperture element (32), can be aligned with the visual axis of the eye (21) to provide a line of sight which passes through the passage opening (33) of the intraocular implant (11) (or the first annular zone or the second annular zone of the intraocular implant). The IOL (8) can then be located inside the lens capsule (45) by conventional methods to overlay the intraocular implant (11) placed in the cavity of the posterior capsule (5).

Figure 43:
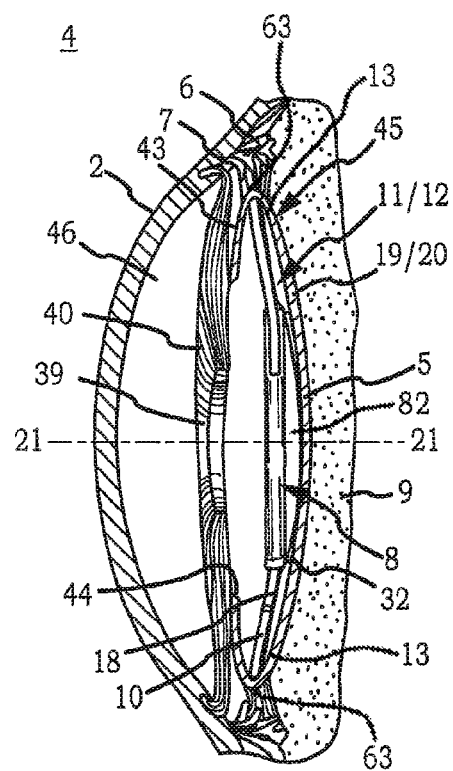
FIG. 43 is a cross section view of the pseudophakic eye having the intraocular implant of FIG. 9 positioned between the surface the posterior capsule and the implanted IOL.

As a non-limiting example, FIG. 43 shows the IOL (8) overlying the intraocular implant (11) with the passage opening (33) of the aperture element (32) centered underneath the IOL (8). If centration of the intraocular implant (11) is not adequate, it can be readily manipulated into position with a Sinskey Hook or similar instrument. Once implanted into the eye, particular embodiments of the biocompatible biodegradable intraocular implant (12) can biodegrade as above described with normal turnover of the fluid of the eye.

Now referring primarily to FIG. 44, a non-limiting example of an embodiment of the intraocular implant (11) shown in FIGS. 6 and 11 having an annular member (74) can be placed in the cavity of the posterior capsule (5) with the edge (80) of the annular member (74) located proximate the outer circumference (63) of the lens capsule (45). The IOL (8) can be located in the lens capsule (45) by conventional methods to overlay the intraocular implant (11) with the haptics (10) engaged with the inside surface (77) of the annular member (74) and the lens of the IOL (8) substantially centered with the visual axis (21).

Now referring primarily to FIG. 45, a non-limiting example of a one-piece intraocular implant (11) as shown in FIGS. 12 and 13 can be placed in the cavity of the posterior capsule (5) with the edge (80) of the annular member (74) located proximate the sulcus of the lens capsule (45). The one piece IOL (8) can be located in the lens capsule (45) by conventional methods to align the lens of the one piece IOL (8) with the visual axis (21).

Now referring primarily to FIG. 45, in those surgical procedures in which the natural crystalline lens (3) is not removed such as retinal surgery, cornea transplant surgery, glaucoma surgery, or the like, or in cataract surgery in which the intraocular implant (11) is not located posterior the IOL (8) (for example, due to posterior capsule tear), the intraocular implant (12) can be placed anterior to the natural lens (3) or the IOL (8) within the ciliary sulcus.

Figure 47:
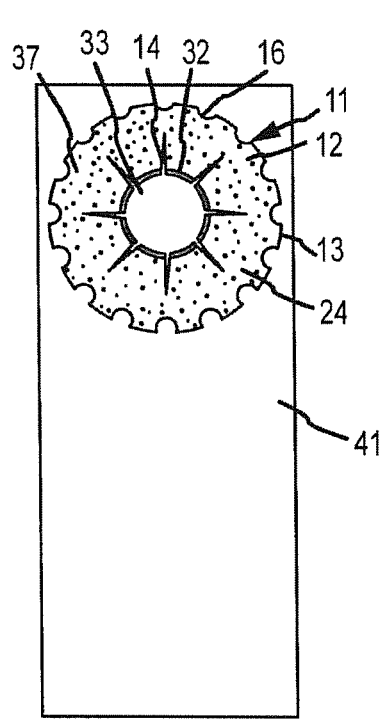
FIG. 47 is front view of an embodiment of the intraocular implant affixed to a sterile card prior to implantation.
Figure 48:
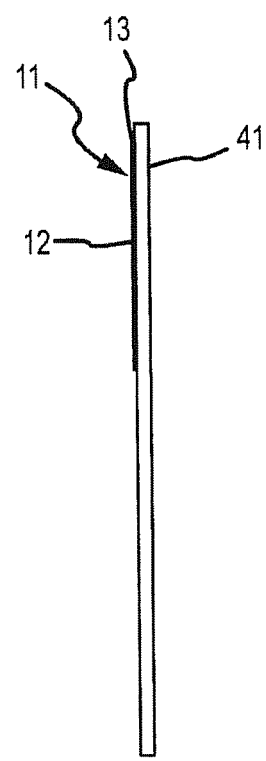
FIG. 48 is a side view of an embodiment of the intraocular implant affixed to a sterile card prior to implantation.

Now referring primarily to FIGS. 47 and 48, the invention can further include a intraocular implant packaging substrate (41) on which embodiments of the inventive intraocular implant (11) can be releasably fixed. The intraocular implant (11) can be removed by manipulation with forceps (38) for use in various applications as above described.

As can be easily understood from the foregoing, the basic concepts of the present invention may be embodied in a variety of ways. The invention involves numerous and varied embodiments of an intraocular implant (11) which as to particular embodiments can be used but is not limited to control of migration of residual lens epithelial cells between the posterior surface of an IOL (8) and the surface of the posterior capsule (5) of the eye to reduce opacification of the posterior capsule (5).

As such, the particular embodiments or elements of the invention disclosed by the description or shown in the figures or tables accompanying this application including the best mode are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of "an implant" should be understood to encompass disclosure of the act of "implanting"—whether explicitly discussed or not—and, conversely, were there effectively disclosure of the act of "implanting", such a disclosure should be understood to encompass disclosure of "an implant" and even a "means for implanting." Such alternative terms for each element or step are to be understood to be explicitly included in the description.

In addition, as to each term used it should be understood that unless its utilization in this application is inconsistent with such interpretation, common dictionary definitions should be understood to included in the description for each term as contained in the Random House Webster's Unabridged Dictionary, second edition, each definition hereby incorporated by reference.

Thus, the applicant(s) should be understood to claim at least: i) each of the intraocular implants herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

The claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

I claim:

1. A method of treating an intraocular condition, comprising:

positioning a biocompatible flexible membrane in a lens capsule inside of an eye for treating said intraocular condition, said biocompatible flexible membrane continuous between flat first and second sides disposed in opposed relation a thickness apart and extending to an outer boundary defining a circular area, and wherein said biocompatible flexible membrane has an aperture element which communicates between said flat first and second sides of said biocompatible flexible membrane to provide a passage opening alignable in a visual axis of said eye;

engaging said second side of said biocompatible flexible membrane with a surface of a posterior capsule of said lens capsule inside of said eye;

engaging said outer boundary of said biocompatible flexible membrane with an outer circumference of said lens capsule to align said passage opening in said visual axis of said eye; and overlaying said first side of said biocompatible flexible membrane having said second side engaged with said surface of said posterior capsule with a lens.

2. The method of claim 1, wherein treating an ocular condition comprises structurally inhibiting migration of target cells into said posterior capsule of said eye by engagement of said second side of said biocompatible flexible membrane with said surface of said posterior capsule.

3. The method of claim 2, further comprising patterned surface elements coupled to at least one of said first and second sides of said biocompatible flexible membrane, said patterned surface elements having dimensional relations adapted to inhibit migration of said target cells into said posterior capsule of said eye.

4. The method of claim 3, wherein treating an ocular condition further comprises pharmaceutically inhibiting migration of said target cells into said posterior capsule of said eye, and wherein said biocompatible flexible membrane includes at least one active agent dispersed in said biocompatible flexible membrane, said biocompatible flexible membrane releasing said at least one active agent in amounts effective to inhibit migration of said target cells into said posterior capsule of said eye.

5. The method of claim 4, wherein said target cells comprise residual lens epithelial cells.

6. The method of claim 5, wherein said active agent is releasable in sufficient amounts to kill said residual lens epithelial cells.

7. A method of treating an intraocular condition, comprising:

positioning a biocompatible flexible membrane in a lens capsule inside of an eye for treating said intraocular condition, said biocompatible flexible membrane continuous between flat first and second sides disposed in opposed relation a thickness apart, and further including an annular member coupled to said first side of said biocompatible flexible membrane, said annular member having an edge defining an outer boundary of a circular area of said biocompatible membrane, and wherein said biocompatible flexible membrane has an aperture element which communicates between said flat first and second sides of said biocompatible flexible membrane to provide a passage opening alignable in a visual axis of said eye;

engaging said biocompatible flexible membrane with a surface of a posterior capsule of said lens capsule inside of said eye;

locating said annular member proximate said outer circumference of said lens capsule to align said passage opening in said visual axis of said eye;

overlaying the biocompatible flexible membrane engaged with said surface of said posterior capsule with a lens.

8. The method of claim 7, wherein said annular member has sufficient height to engage haptics connected to said lens engaged with a first side of said biocompatible flexible membrane, and further comprising engaging said haptics connected to said lens with said annular member.

9. The method of claim 6, wherein said biocompatible flexible membrane comprises a biodegradable biocompatible flexible membrane.

10. The method of claim 9, wherein said biodegradable biocompatible flexible membrane further comprises a plurality of radial slit elements each of which originate at said aperture element extending radially outward toward said outer boundary, said plurality of radial slit elements biasing at a rate at which said biodegradable biocompatible flexible membrane biodegrades, wherein said biodegradable biocompatible flexible membrane biodegrades at a greater rate proximate said aperture element and at a lesser rate proximate said outer boundary, thereby biodegrading said biodegradable biocompatible flexible membrane directionally from said aperture element toward an outer boundary.

11. The method of claim 9, wherein said biodegradable biocompatible flexible membrane comprises a first flexible membrane layer and a second flexible membrane layer, and wherein said first flexible membrane layer biodegrades at a greater rate than said second flexible membrane layer, thereby biodegrading said biodegradable biocompatible flexible membrane directionally from said first flexible membrane layer toward said second flexible membrane layer.

12. The method of claim 9, wherein said biodegradable biocompatible flexible membrane comprises a first annular zone of said biodegradable biocompatible flexible membrane and a second annular zone of said biodegradable biocompatible flexible membrane, and wherein said first annular zone of said biodegradable biocompatible flexible membrane biodegrades a greater rate than said second annular zone, thereby biodegrading said biodegradable biocompatible flexible membrane directionally from first annular zone toward said second annular zone.

13. The method of claim 9, wherein said biodegradable biocompatible flexible membrane further comprises a plurality of perforation elements which communicate between opposed sides of said biodegradable biocompatible membrane thereby increasing the rate at which said biodegradable biocompatible flexible membrane degrades.

14. The method of claim 11, wherein releasing said at least one active agent in amounts effective to inhibit migration of said target cells into said posterior capsule of said eye, comprises the steps of:

releasing a first active agent from a first flexible membrane layer of said biodegradable biocompatible flexible membrane; and releasing a second active agent from a second flexible membrane layer of said biodegradable biocompatible flexible membrane.

15. The method of claim 12, wherein said step of releasing said at least one active agent in amounts effective to inhibit migration of said target cells into said posterior capsule of said eye, comprises the steps of:

releasing a first active agent from a first annular zone of said biodegradable biocompatible flexible membrane; and releasing a second active agent from a second annular zone of said biodegradable biocompatible flexible membrane.

16. The method of claim 9, wherein said biodegradable biocompatible flexible membrane further comprises a plurality of corrugate elements in said biocompatible biodegradable flexible membrane, said corrugate elements configured to allow fluid within said eye to circulate between said biodegradable biocompatible flexible membrane and a surface of said posterior capsule of said eye.

17. The method of claim 9, wherein said biodegradable biocompatible flexible membrane further comprises a plurality of radial capillaries which communicate between said outer boundary and said aperture element, said plurality of radial capillaries configured to allow fluid within said eye to circulate between said first side of said biodegradable biocompatible flexible membrane and said surface of said posterior capsule of said eye.

18. The method of claim 8, wherein treating an ocular condition comprises structurally inhibiting migration of target cells into said posterior capsule of said eye.

19. The method of claim 18, wherein said biocompatible flexible membrane further comprises patterned surface elements coupled to at least one of said first and second sides of said biocompatible flexible membrane, said patterned surface elements having dimensional relations adapted to inhibit migration of said target cells into said posterior capsule of said eye.

20. The method of claim 8, wherein treating an ocular condition further comprises pharmaceutically inhibiting migration of said target cells into said posterior capsule of said eye, and wherein said biocompatible flexible membrane includes at least one active agent dispersed in said biocompatible flexible membrane, said biocompatible flexible membrane releasing said at least one active agent in amounts effective to inhibit migration of said target cells into said posterior capsule of said eye.

21. The method of claim 20, wherein said target cells comprise residual lens epithelial cells.

22. The method of claim 21, wherein said active agent is releasable in sufficient amounts to kill said residual lens epithelial cells.

\* \* \* \* \*